(12) United States Patent
Imran

(10) Patent No.: US 10,264,987 B2
(45) Date of Patent: *Apr. 23, 2019

(54) METHOD FOR THE DETECTION AND TREATMENT OF ABERRANT NEURAL-ELECTRIC ACTIVITY

(71) Applicant: InCube Labs, LLC, San Jose, CA (US)

(72) Inventor: Mir Imran, Los Altos Hills, CA (US)

(73) Assignee: INCUBE LABS, LLC, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/917,627

(22) Filed: Jun. 13, 2013

(65) Prior Publication Data

US 2013/0281811 A1 Oct. 24, 2013

Related U.S. Application Data

(60) Continuation of application No. 13/301,584, filed on Nov. 21, 2011, now Pat. No. 8,467,877, which is a
(Continued)

(51) Int. Cl.
*A61N 1/05* (2006.01)
*A61B 5/04* (2006.01)
(Continued)

(52) U.S. Cl.
CPC ...... *A61B 5/04001* (2013.01); *A61B 5/04004* (2013.01); *A61B 5/0478* (2013.01);
(Continued)

(58) Field of Classification Search
CPC .................. A61N 1/05; A61N 1/0529–1/0539
(Continued)

(56) References Cited

U.S. PATENT DOCUMENTS 5,237,996 A * 8/1993 Waldman et al. ............ 600/374
5,551,426 A * 9/1996 Hummel et al. ............. 600/374
(Continued)

FOREIGN PATENT DOCUMENTS

WO WO 2008/068759 6/2008
WO WO 2010/085782 7/2010

OTHER PUBLICATIONS

International Search Report, Written Opinion, and Notice of Transmittal of Same dated Aug. 26, 2010 in International App. PCT/US2010/022051.
(Continued)

*Primary Examiner* — George R Evanisko
(74) *Attorney, Agent, or Firm* — Mahamedi IP Law LLP; Joel Harris

(57) ABSTRACT

An apparatus for detection of ANEA comprising an introducer having at least one lumen. The introducer is introduced into brain tissue through an opening in the skull. A reference electrode is positioned at an introducer distal portion. A plurality of electrode members are advanceable within the at least one lumen with each member having an insulated portion and an exposed distal portion. The members have a non-deployed state in the introducer and a deployed state when outwardly advanced out of the introducer. In the deployed state, the members are substantially orthogonal to each other with the exposed distal portions defining a detection volume capable of determining an electric field vector produced by the ANEA and the direction of foci of the ANEA.

19 Claims, 24 Drawing Sheets

Related U.S. Application Data division of application No. 12/359,830, filed on Jan. 26, 2009, now Pat. No. 8,374,703.

(51) Int. Cl.
 *A61B 5/0478* (2006.01)
 *A61B 5/00* (2006.01)
 *A61B 5/053* (2006.01)
 *A61N 1/36* (2006.01)

(52) U.S. Cl.
 CPC .......... *A61B 5/4094* (2013.01); *A61B 5/0531* (2013.01); *A61N 1/0529* (2013.01); *A61N 1/0539* (2013.01); *A61N 1/36017* (2013.01); *A61N 1/36025* (2013.01); *A61N 1/36064* (2013.01); *A61N 1/36082* (2013.01)

(58) Field of Classification Search
 USPC ................................................ 607/3, 45, 116
 See application file for complete search history.

(56) References Cited

U.S. PATENT DOCUMENTS

| | | | |
|---|---|---|---|
| 5,713,923 | A | 2/1998 | Ward et al. |
| 6,016,449 | A | 1/2000 | Fischell et al. |
| 6,353,762 | B1 * | 3/2002 | Baudino et al. ................. 607/45 |
| 7,006,859 | B1 | 2/2006 | Osorio et al. |
| 7,181,288 | B1 * | 2/2007 | Rezai et al. .................. 607/116 |
| 7,831,308 | B2 * | 11/2010 | Rezai et al. .................... 607/48 |
| 8,374,703 | B2 | 2/2013 | Imran |
| 8,467,877 | B2 | 6/2013 | Imran |
| 2002/0062143 | A1 | 5/2002 | Baudino et al. |
| 2004/0199235 | A1 * | 10/2004 | Younis .......................... 607/116 |
| 2005/0182453 | A1 | 8/2005 | Whitehurst et al. |
| 2006/0025387 | A1 | 2/2006 | Hochman |
| 2006/0122677 | A1 | 6/2006 | Vardiman |
| 2007/0060973 | A1 | 3/2007 | Ludvig et al. |
| 2007/0150024 | A1 | 6/2007 | Leyde et al. |
| 2007/0150025 | A1 | 6/2007 | Dilorenzo et al. |
| 2009/0317387 | A1 | 12/2009 | Paton et al. |
| 2010/0063071 | A1 | 3/2010 | Kiesman et al. |

OTHER PUBLICATIONS

Non-Final Office Action dated Dec. 29, 2011 in U.S. Appl. No. 12/359,830.
Non-Final Office Action dated May 22, 2012 in U.S. Appl. No. 13/301,584.
International Preliminary Report on Patentability dated Aug. 4, 2011 in PCT/US2010/022051.
Office Action dated Apr. 3, 2013 in Chinese Application 201080008430.8.
First Examination Report dated Aug. 27, 2013 in Australian Application No. 2010206520.
Notice of Allowance dated Feb. 5, 2013 in U.S. Appl. No. 13/301,584.
Notice of Allowance dated Sep. 17, 2012 in U.S. Appl. No. 12/359,830.

* cited by examiner

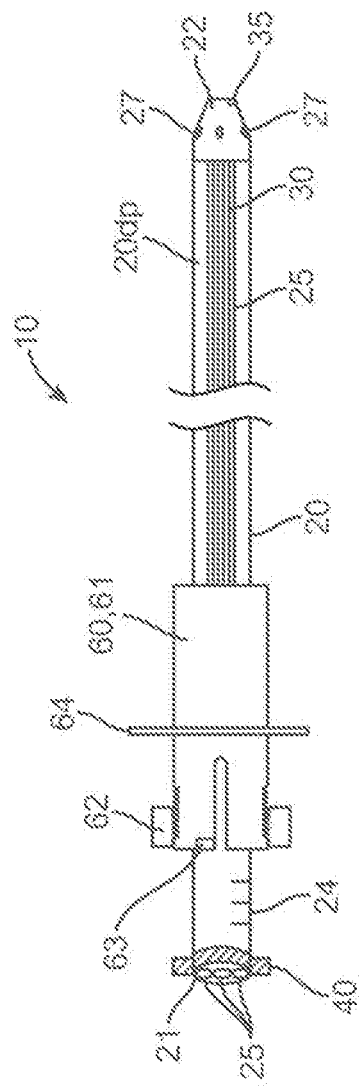
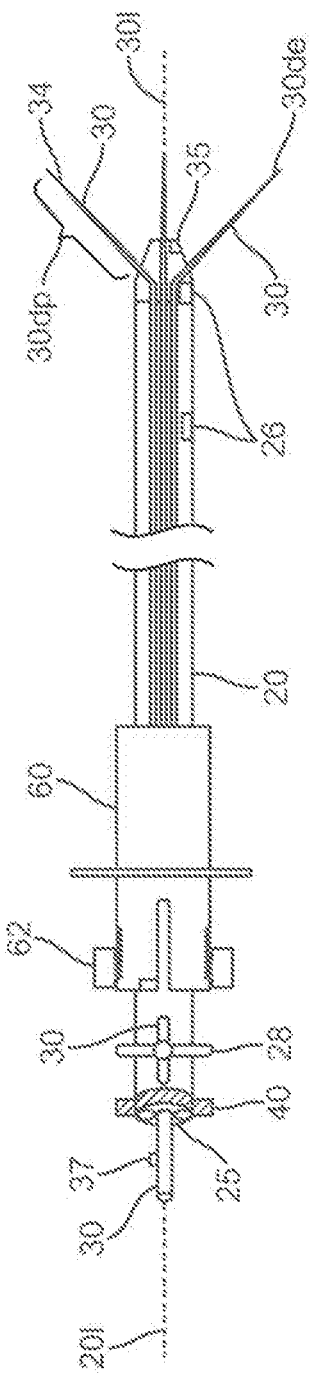
FIG. 6a
FIG. 6b

Normal Brain Activity

Brain Activity During a
Pre-Seizure or Seizure Event

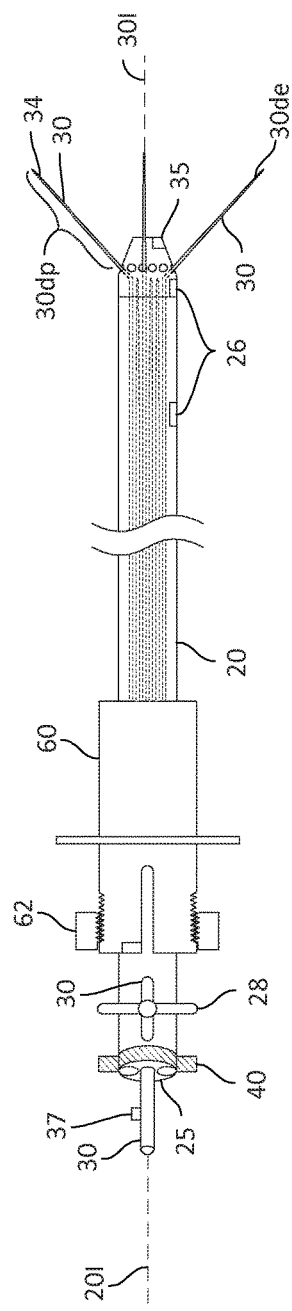
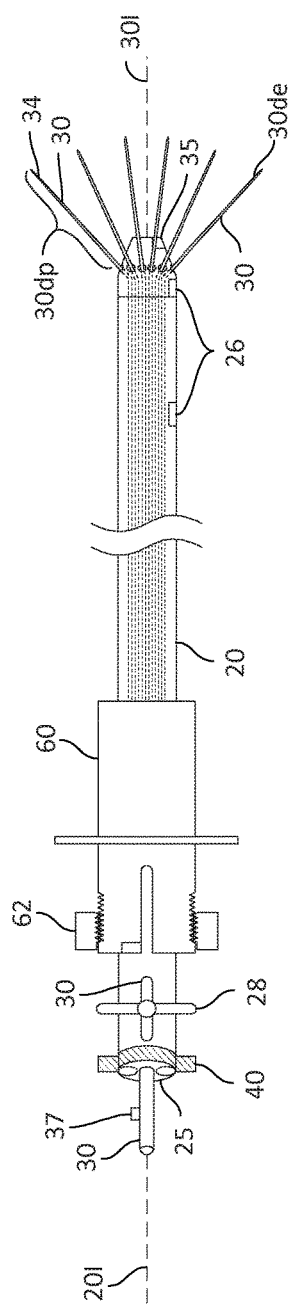

METHOD FOR THE DETECTION AND TREATMENT OF ABERRANT NEURAL-ELECTRIC ACTIVITY

RELATED APPLICATIONS

This application is a continuation of U.S. patent application Ser. No. 13/301,584 filed Nov. 21, 2011 and issued as U.S. Pat. No. 8,467,877 on Jun. 18, 2013, entitled "METHOD FOR THE DETECTION AND TREATMENT OF ABERRANT NEURAL-ELECTRIC ACTIVITY" which is a divisional of U.S. patent application Ser. No. 12/359,830 filed Jan. 26, 2009 and issued as U.S. Pat. No. 8,374,703 on Feb. 12, 2013, entitled "METHOD AND APPARATUS FOR THE DETECTION OF ABERRANT NEURAL-ELECTRIC ACTIVITY"; the aforementioned applications are hereby incorporated by reference herein in their entireties for all purposes.

FIELD OF THE INVENTION

Embodiments described herein provide a system apparatus and method for detecting and treating epilepsy and other conditions characterized by aberrant neural-electric activity using implanted electrodes.

BACKGROUND

There are a number of neurological events and conditions which are characterized by abnormal neural-electric activity in the brain including epilepsy, migraine headaches and even some forms of depression. Epilepsy is a disease characterized by recurrent unprovoked seizures which result in episodic impairment or loss of consciousness, abnormal motor phenomena, psychic or sensory disturbances, or the perturbation of the autonomic nervous system. It is caused by abnormal firing of neurons in the brain, a condition known as epileptogensis. These abnormal firings or electrical discharges may start in small neuronal populations (these are known as epileptogenci foci, the condition defined as focal epilepsy) or much larger areas of the brain (this condition is defined as generalized epilepsy). Often there can be a period of abnormal firing of neurons which precedes the full blown seizure. This period is known as a pre-seizure state and it can include one or more events of abnormal firing, known as pre-seizure events.

Whatever the cause, the human and financial impact of the disease is significant. The prevalence of epilepsy in the US is currently about three million world wide about fifty million with 200,000 new cases diagnosed each year in the US alone. Ten percent of the American population will experience a seizure in their lifetime. Due to the impairing nature of epileptic seizures, the disease can prevent patients from performing a number of routine activities including driving car or operation of machinery. Many states put driving restrictions on those diagnosed with epilepsy. In a sub-population of patients, the severity of the disease is so extreme that they are essentially incapacitated. The economic cost of the disease is estimated to be $12.5 billion per year in direct and indirect costs.

While there are a number of available drug therapies, these therapies have a number of side effects including hyperplasia, slurred speech and memory loss. They also require precise control of the therapeutic dosage to avoid occurrence of seizures for too low a dose or side effects for too high a dose. Also estimates are that at least 20-30 percent of epilepsy patients can not be effectively treated with currently available drug therapies. In patients populations having medically refractory epilepsy with partial-onset seizures are known not to respond well to anti seizure medication. The only option for these and other patients is radical brain surgery which presents significant morbidity mortality issues as wells as being contraindicated in a number of cases. While there have been various attempts at using electrical stimulation of the brain, particularly deep brain stimulation as a means of treating the disease, these approaches are limited to the use of continuous stimulation and do not employ detection means so as modulate or otherwise modify the stimulation responsive a change in the patient's brain activity. Also continuous deep brain stimulation has several drawbacks. To be effective, the treatment may require stimulation of neocortex which is often the origin or focus of epileptic seizures. However continuous or frequent stimulation in this region may cause various neurological symptoms including speech impairment, sensory impairment, involuntary motion memory loss and depression. Also the foci can originate in a number of areas of the brain, not just the neocortex, including the cerebral cortex, primary motor cortex, premotor cortex hippocampus, to name a few. Thus stimulating only the neo-cortex may not be effective.

While several approaches have been employed for localization of epileptic foci using electroencephalogram measurements (EEG) these have largely relied on surface electrodes which also have drawbacks. These include very weak signals when epileptogenic foci are located in deep brain tissue, when there are two or more foci which can cancel each other out (due to the dipole nature of the signal) or closed field foci (due to the foci being located in a sheet of non-parallel tissue. Other draw backs with surface electrodes include the tendency of the various tissue layers which overly the foci (e.g., the meninges, bone, skin, etc) to spread out the signal over a larger layer of the scalp making localization difficult and the fact that dipoles generated by the foci can oriented be parallel or obliquely to the electrodes causing phase reversal and false localization of the signal. Many of these same issues including difficulties in localization and phase reversal can also occur for an implanted electrode. These issues can make detection of pre-seizure events leading to a seizure even more difficult since the magnitude and duration of aberrant neural electric activity during the pre-seizure event can be reduced compared to an actual seizure.

Accordingly, a need exists for devices and methods for detecting seizure or pre-seizure events/states so that acute treatment (e.g., drug or stimulation) can be delivered to prevent the seizure and/or minimize it's effects. Also since the foci of an epileptic seizure can originate in variety of areas of the brain, there is a need for devices and methods that are capable of detecting the onset of an epileptic event no matter where the foci are located.

BRIEF SUMMARY

Embodiments described herein provide a system apparatus and method for detecting epilepsy and other condition characterized by aberrant neural-electric activity using implanted electrodes. Many embodiments provide an apparatus and method for detecting epilepsy using an implanted device having orthogonally oriented electrode members configured to be able to detect and locate the direction of aberrant neural-electric activity in the brain. Specific embodiments can detect an electric field vector generated by a foci or other origin of aberrant neural-electric activity and use this information to detect the onset of an epileptic seizure or events predictive of the onset of an epileptic seizure.

One embodiment provides an apparatus for detection of aberrant neural-electric activity in the brain such as that from epilepsy comprising an introducer having a proximal end a distal end, and a plurality of lumens with a port coupled to each lumen. The introducer is configured to be introduced into brain tissue through a burr hole or other opening in the skull. In many embodiments, the introducer can itself be introduced through a burr hole plug or a like device which is inserted into the opening in the skull. Typically, the plug will also include a locking device such as a clamp which locks or fixes the introducer to the plug so that the introducer does not move once inserted. The lock and the clamp can contain sensors to detect movement of the introducer or otherwise detect an unlocked state of the introducer. The ports are typically positioned at a distal portion of the introducer, with the proximal end configured to be coupled to an electrical connector. The connector can be coupled to circuitry and processors having one or more signal processing circuits and algorithms for analyzing signals received by the electrode members. A reference electrode is positioned at distal portion of the introducer. Three or more electrode members are advanceable within the plurality of lumens with each electrode member having an insulating jacket extending along a length of the electrode member to leave a distal portion of the electrode member exposed. Embodiments having four, six or nine electrodes are also contemplated. Each electrode member has a non-deployed state when contained in the introducer and a deployed state when advanced outside of introducer. When the electrode members are in the deployed state, they are configured to be substantially orthogonal to each other, though other arrangements are also contemplated. This orthogonal relationship can be achieved through the spatial arrangement of the ports which themselves can be substantially orthogonal.

Typically, a distal portion of the electrode is preformed to have a bent shape when in the deployed state. The bend can include angles of 30, 45 and 60° and can be achieved through the use of one or more shape memory metals. Desirably, the electrode members have a stiffness configured to be advanced into brain tissue and maintain their bent shape as well as the size and shape of the detection volume defined below. The stiffness of the electrode members together with their bent shape can also be used to anchor or otherwise stabilize the position of the electrode members when they are deployed in brain tissue. Additionally, the size and shape of the electrode members is such that they have minimal physiological effect on the brain tissue in which they are deployed including for example foreign body response and effect on normal neural-electric activity of the brain. Similarly, the conductive surface area of the electrodes members is configured to have a minimal effect on neural-electric activity of the brain. In various embodiments, the length of the electrode member advanced into tissue can range from about 0.1 to 3 cm with preferred embodiments in the range from about 0.5 to 1.5 cms.

The bend of the electrode member is such that the exposed distal portions of the electrode member define a detection volume capable of determining the direction of a foci of epileptogenic or other aberrant neural-electric activity. Typically, the detection volume will have a tetrahedral shape though other shapes are also contemplated. The shape and size of the detection volume can be matched to the particular location and characteristics of the aberrant neural-electric activity or other disease characteristic (e.g., partial onset seizures) which are determined in advance.

The arrangement of the electrode members in combination with the detection volume can be configured to determine an electric field vector generated by the aberrant neural-electric activity. Typically, the arrangement is orthogonal with the three electrodes projecting out of the introducer so as to define a three dimensional Cartesian coordinate system with the reference electrode positioned a distal end of the introducer or other location so as to be at the origin of the coordinate axis. By knowing the length of the exposed electrode member, the magnitude of the electric field vector in each of the three axis can be determined (using vector and trigonometric calculations) which in turn can be used to determine the entire field vector (both magnitude and direction).

In various embodiments, the introducer can include a deflector configured to the deflect the electrode members as they are advanced distally out of the ports such that they have a bent shape such that the exposed distal portions define the detection volume. In such embodiments, the introducer need only have one lumen through which the electrode members are advanced with the deflector positioned at a distal portion of the lumen so that it deflects the electrode members as they are advanced out of the lumen.

Various embodiments of the invention also provide methods for detecting aberrant neural-electric activity (ANEA) such as that preceding or occurring during an epileptic seizure, migraine or other related neurological event or condition. More specifically, embodiments provide methods for detecting a foci of ANEA including detecting the direction and location of such foci relative using that information to predict the onset of an epileptic seizure, migraine, or other neurological events. In exemplary method embodiment of the invention, a plurality of orthogonally deployed electrodes described herein are used to detect and calculate an electric field vector generated by the foci of ANEA and use that information to determine the direction of the foci relative to the deployed electrodes. Signal processing and other algorithms can then be employed to analyze the location, magnitude and frequency characteristics of the electric field vector and neural-electric signals and waveforms generated by the ANEA foci and make a prediction on whether an epileptic seizure or migraine or other neurological event or condition is occurring or is about to occur. The prediction can be based on comparison of the detected signals and waveforms to a database of waveforms characteristic of signals and waveforms preceding or occurring during an epileptic seizure or other neurological event or condition. Upon determination that an epileptic seizure is about to occur or is occurring, signals can then be sent to an alarm in an external monitoring device to alert the patient to take appropriate medication; they can also be wirelessly communicated to a medical health professional over a cellular phone network. Additionally, upon detection of such events, the patient can be given electrical stimulation (using the same or a different set of electrode members) that is configured to prevent or lessen the seizure duration. Concurrent or separate to such stimulation, the patient can also be automatically given anti-seizure medication which is delivered intra-cranially (through a burr hole in the scalp such as that used for the detection apparatus) or intravenously or both. The dose can be in the form of a bolus to achieve a peak intracranial concentration as well as longer term intracranial or IV dose. The intracranial or IV delivery can be achieved through an external drug pump worn by the patient. Alternatively, the delivery can also be achieved through means of a drug pump implanted under the scalp, in the neck or other nearby region.

In various methods for placement of the detection apparatus within the brain, prior to implantation a patient having an epilepsy or other condition characterized by ANEA can undergo a series of EEGs or other related scans to determine the location and other characteristics of the foci of ANB-NEA likely causing their epilepsy. That information can then be used to guide or otherwise in the placement of the detection apparatus in the brain. Specifically the deployed electrodes can be placed in a location close to the foci. This can improve the sensitivity and accuracy of the apparatus in detecting ANEA caused by the foci. Additionally, the shape of the deployed electrodes including the detection volume defined by the electrodes can be adjusted relative to the location and signal characteristics of the foci so as to improve both the sensitivity and accuracy for detection of ANEA.

Further details of these and other embodiments and aspects of the invention are described more fully below, with reference to the attached drawing figures.

BRIEF DESCRIPTION OF THE DRAWINGS

FIGS. 4a-4b are perspective views and FIG. 4c is a frontal cross-sectional view.

FIG. 6a is side view showing an embodiment of the ANEA detection apparatus with the electrode members in the non deployed state inside the introducer.

FIG. 6b is side view showing an embodiment of the ANEA detection apparatus with the electrode members in advanced out of the introducer in a deployed state.

FIG. 8a shows an embodiment of an electrode having an abrupt bend, FIG. 8b shows an embodiment having a curved bend.

FIG. 10a illustrates an electrode member having a solid conductive core, while FIG. 10b illustrates an electrode member having at least one lumen.

FIG. 16a shows the burr hole opening in the skull. FIG. 16b shows placement of a burr hole plug in the burr hole opening. FIG. 16c shows the introduction and advancement of the introducer through the burr hole plug. FIG. 16d shows the full advancement of the introducer. FIG. 16e shows the deployment of the electrode members to a configuration for detecting the Foci.

FIG. 17a is over a period of normal activity and FIG. 17b is over a period of aberrant neural-electric activity in the brain.

FIGS. 19A and 19B illustrate side views of an ANEA detection apparatus utilizing individually advanceable electrode members to obtain a selectable detection volume, under an embodiment.

DETAILED DESCRIPTION OF THE INVENTION

Various embodiments described herein provide a system, apparatus and method for detecting various neurological events ord conditions such as epilepsy which are characterized by aberrant neural-electric activity. Many embodiments provide an apparatus and method for detecting aberrant neural-electric activity prior to the actual physical manifestation of the event or condition caused by the neural-electric activity (e.g. detect electrical activity prior to occurrence of an epileptic seizure, migraine or other neurological event or condition). In an embodiment, a device is implanted that includes suitably oriented electrode members that are configured to be able to detect and locate the direction of aberrant neural-electric activity in the brain. Specific embodiments can detect and interpret an electric field generated by a foci or other origin of aberrant neural-electric activity. In an embodiment, such information is determined and interpreted as a marker to the onset of an epileptic seizure or other neurological event or condition.

Still further, embodiments described herein provide for detection of aberrant neural-electric activity (ANEA) in a brain of a patient that is likely to cause an epileptic pre-seizure event or a seizure event. In an embodiment, an electric field that is caused or otherwise associated by the ANEA is detected from inside the brain or skull of the patient. An electric field vector characteristic is determined from the electric field. The electric vector is interpreted as being a marker to epileptic pre-seizure event or seizure event. The marker may correspond to a characteristic that is likely to be a precursor to the seizure. According to one or more embodiments, detecting the electrical field may be in form of detecting voltage (or current) on electrodes that are in the skull or brain at the time of ANEA.

Figure 1:
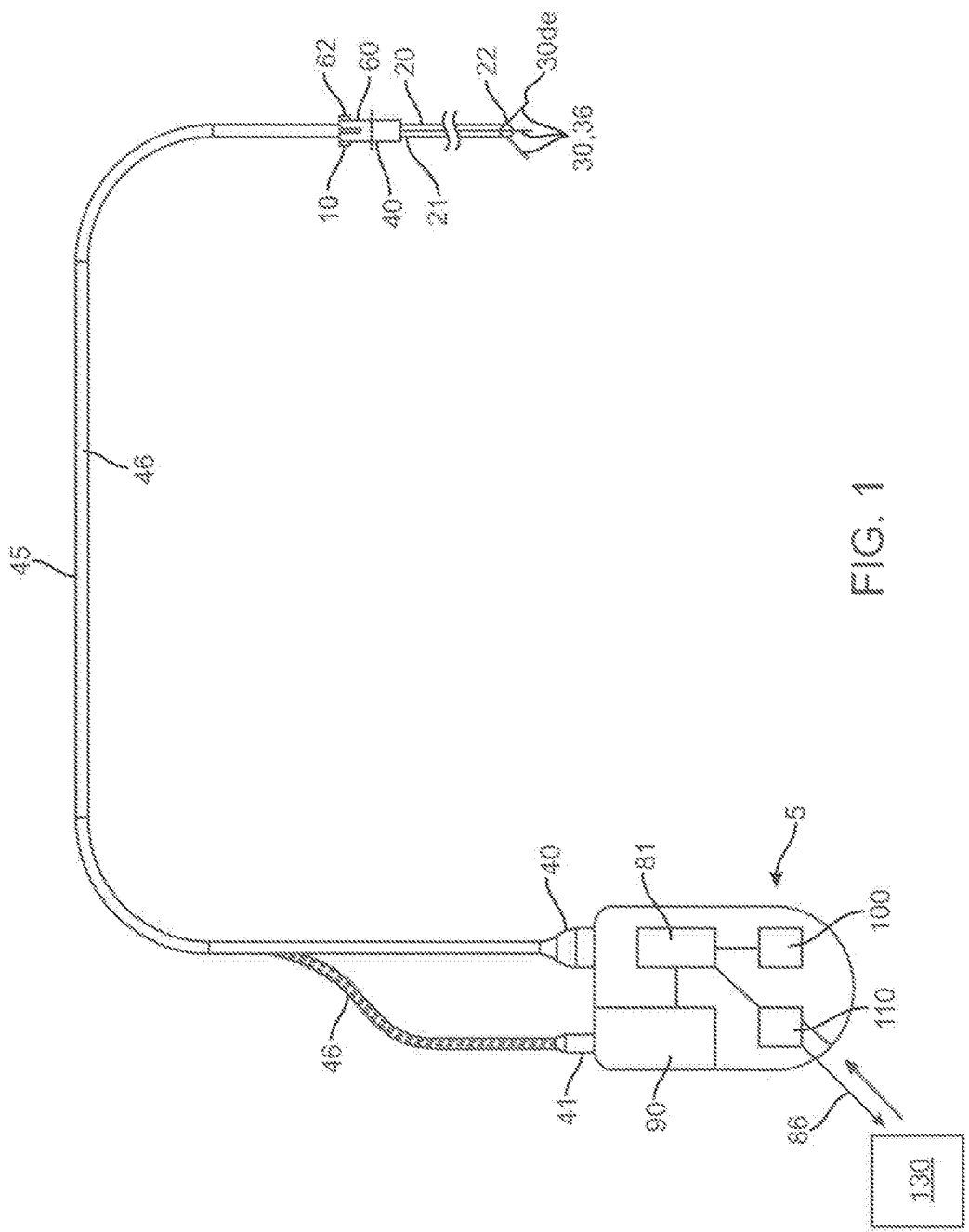
FIG. 1 is a plan view of an embodiment of a system and apparatus for detection of aberrant neural-electric activity (ANEA).
Figure 2A:
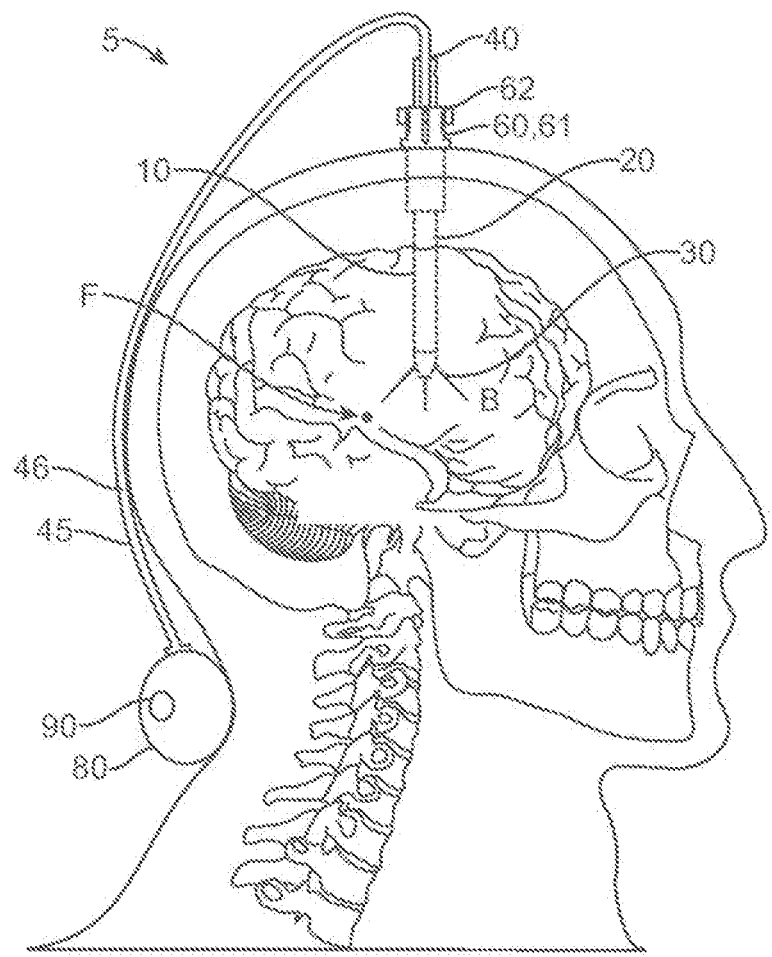
FIG. 2a is a side view showing placement and use of the system and apparatus from the embodiment of FIG. 1 to detect aberrant neural-electric activity in the brain.
Figure 2B:
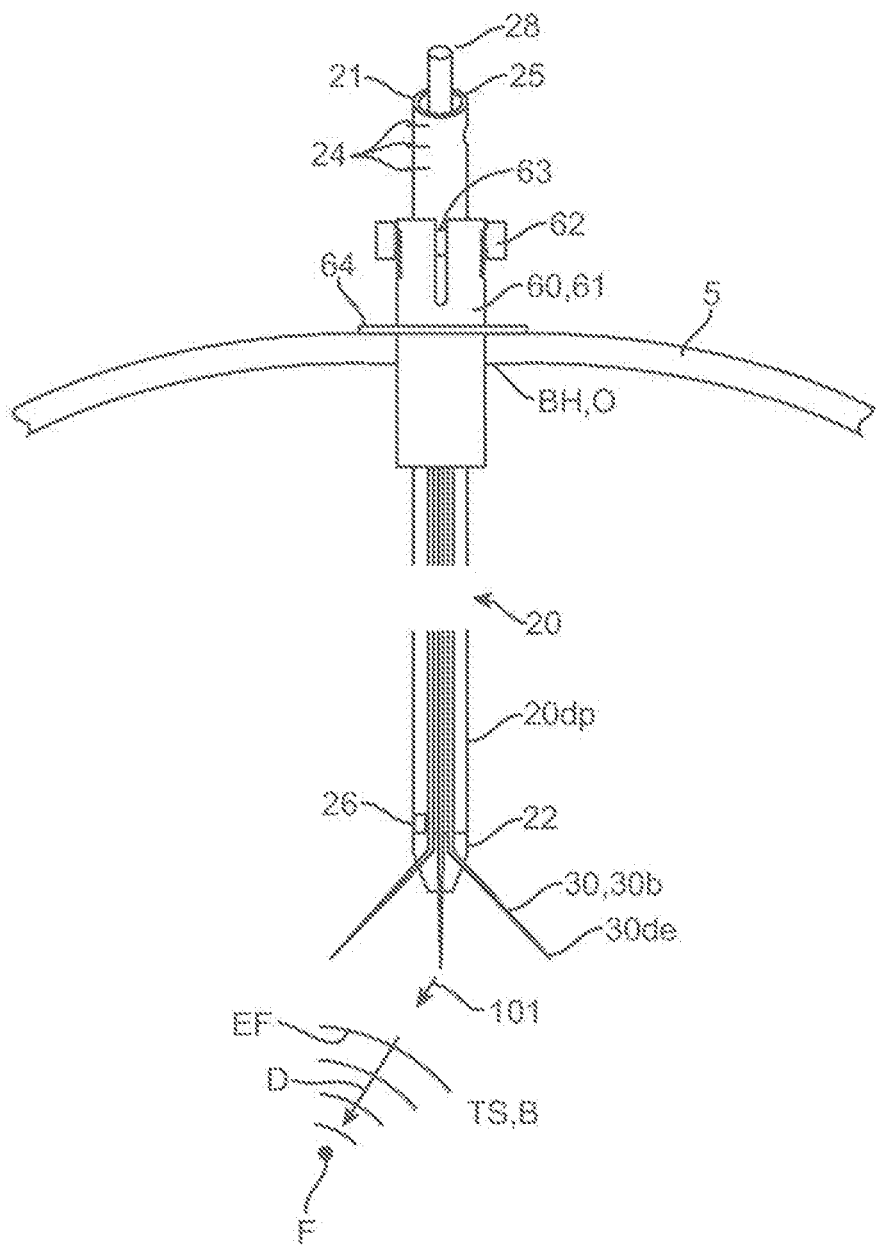
FIG. 2b is a side view showing placement of the plug in burr hole in the skull and the introduction of the ANEA detection apparatus at tissue site in the brain.
Figure 3:
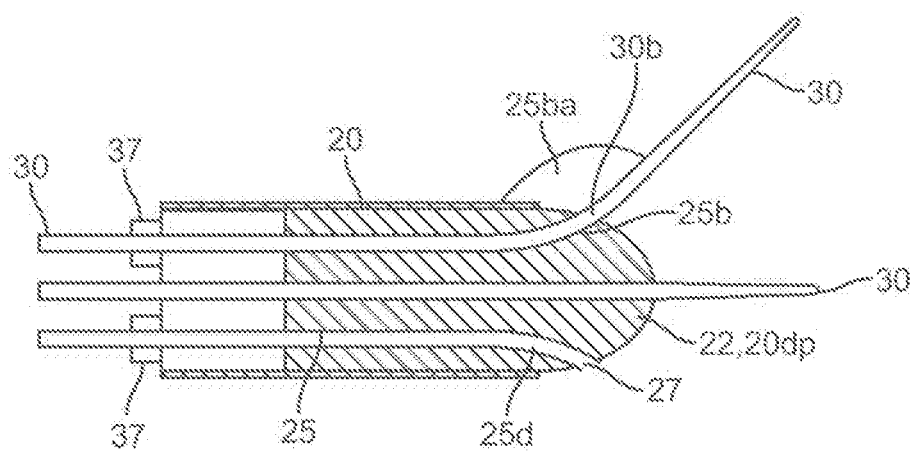
FIG. 3 is cut away side view of a distal portion of the deployed electrode members illustrating use of bent lumens in the introducer to deflect electrode members.
Figure 4A:
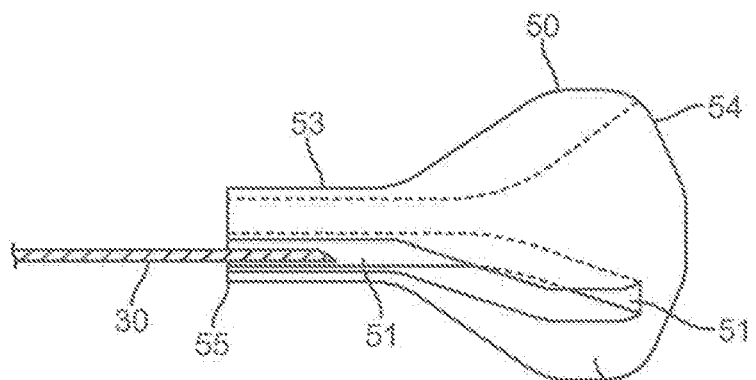
FIGS. 4a-4c are various views showing embodiments of a deflection fixture positioned within the introducer to deflect the electrode members.
Figure 4B:
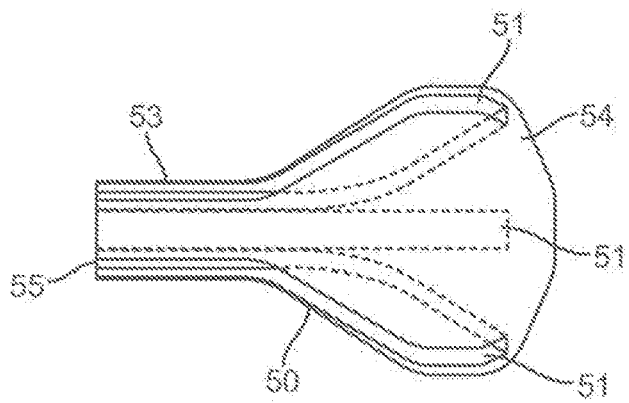
Figure 4C:
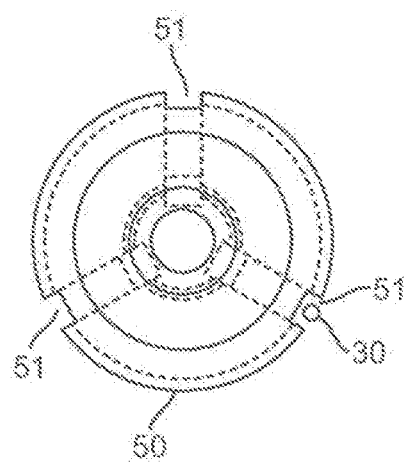
Figure 5:
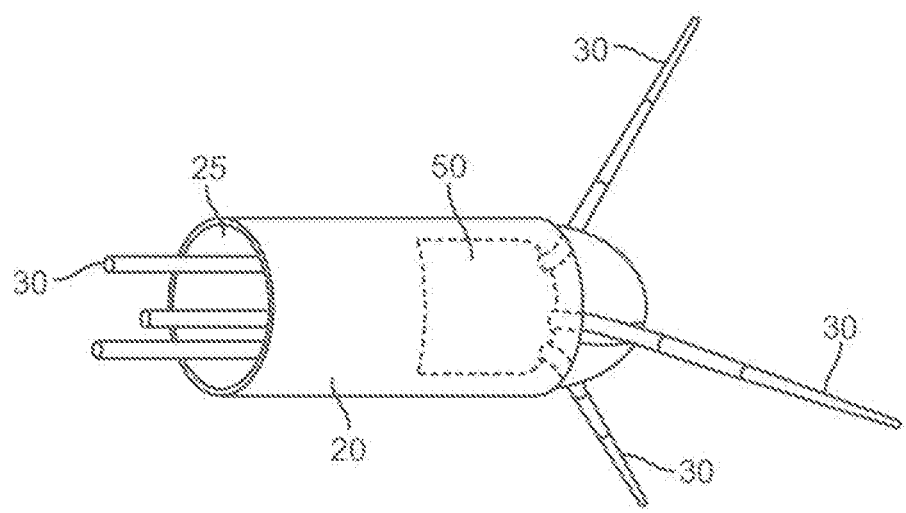
FIG. 5 is a perspective view showing the electrode members existing from the deflector.

Referring now to FIGS. 1-3, various embodiments provide for a system 5 and apparatus 10 for detection of aberrant neural-electric activity (ANEA). System 5 comprises apparatus 10 and a control module 80 described herein. Apparatus 10 includes an introducer 20 having one or more lumens 25, a reference electrode 35 and a plurality of electrode members 30 which are advanceable in lumens 25 to be deployed into brain tissue. Electrode members 30 have a non-deployed state when positioned in the introducer and a deployed state when advanced out of the introducer. In the deployed state, the electrode members can have a bent shape 30B. This bent shape can be used to define a detection volume DV for detection of a Foci F of ANEA.

Introducer 20 has proximal and distal ends 21 and 22 and is configured to be inserted into the skull S of a patient so as to position the electrode members 30 at a target tissue site TS in the brain B. Proximal end 21 can be configured to be coupled to one or more electrical, fluidic or other connectors 40. Embodiments of electrical connectors 40 can include standard connectors such as USB and Firewire connectors and can be configured to be coupled to external processors, A/D converters and like circuitry. Connectors 40 can also comprise a communication port such as an RF or infrared port. In many embodiments, connector 40 is configured to be coupled to external control module 80. In these and related embodiments, connector 40 can be coupled to module 80 via a connecting member 45 which can include electrical wiring and one or more lumens 46 for delivery of fluids including drug containing fluids.

In various embodiments, introducer 20 can be configured to be directly introduced into brain tissue through an opening O in the skull S, or it can be introduced via means of a plug or other skull portal device 60 such as a burr hole plug 61 which is configured to be placed and secured into a burr hole BH (as shown in FIGS. 2a and 2b). Typically, plug 60 includes a locking device 62 such as a clamp or other fixation mechanisms which locks or fixes introducer 20 to the plug 60 so that introducer 20 does not move after insertion. Introducer 20 can also be stabilized by a flange 64 on plug 60 (or other suitable structure or mechanism). One or more of the plug, introducer or locking device can contain a sensor 63 to detect movement of the introducer or otherwise detect an unlocked state of the introducer or if it has otherwise become loose. Suitable sensors 63 include contact sensors, hall effect switches, accelerometers and like devices. Sensors 63 can be coupled to circuitry in control module 80 discussed herein to alert the patient or medical care giver if introducer 20 is no longer in a fixed state. This circuitry can include various filters (e.g., low pass, high pass, etc.) to filter out movement attributed to normal head and body motion from movement attributed to the loosening of introducer 20 from the locking device 62.

Distal introducer end 22 may be configured with a tapered, or other related shape and can be tissue penetrating to facilitate introduction into brain tissue. The introducer may also be configured to track over a guide wire (not shown) which is advanced through a lumen 25 so as to facilitate placement of the distal end 22 at a selected target tissue site TS in the brain. Placement at the target site TS can also be facilitated by use of one or more radio-opaque or echogenic markers 26 which can be positioned at one or more locations on the introducer including distal end 22. Markers 26 allow the introducer to be advanced under fluoroscopic observation or other imaging modality. All or a portion of introducer 20 can comprise various biocompatible polymers known in the art including without limitation polyethylene, PET, PEBAX, PTFE, silicone, polyurethane and combinations thereof. These materials can also comprise one more radio-opaque materials known in the art including titanium dioxide.

As shown in greater detail by FIG. 3, introducer 20 includes one or more lumens 25, which can be configured for advancement of electrode members 30, guide-wires, viewing scopes, lights sources and like devices. Lumens 25 can also be configured for providing suction as well as infusion of various solutions including one or more medicaments solutions for treatment of epilepsy, migraine and other brain related conditions and diseases. Each lumen 25 can also include a port 27 positioned at distal portion 20 $dp$ of introducer to allow for the passage of electrode member 30, as well as fluids and medicaments. In many embodiments, the introducer can include separate lumens 25 for each electrode member 30. This allows for independent advancement of electrode members 30. As is discussed herein, in many embodiments, the distal portion of members 30 can include a bend or curve $30b$. This can be achieved by configuring the distal portion $25d$ of lumens 25 to have an internal bend $25b$ which can correspond to the amount of desired bend in member 30. In various embodiments, the angle $25ba$ of bend $25b$ can be in the range from 20 to 90°, with specific embodiments of 30, 40, 45, 50, 60, 70 and 80°.

Referring now to FIGS. 4A, 4B, 4C and 5, one or more embodiments provide that all or portion of electrode members 30 are advanceable in a single lumen 25. In these and related embodiments, the bend $30b$ in members 30 can be achieved through use of a deflector 50 which deflects the electrode members as they are advanced out of the introducer. Typically, deflector 50 will be positioned in distal portion $25dp$ of lumen 25 but it can also be positioned in other locations as well. Deflector 50 comprises a series of individual channels 51 which direct electrode members 30 at a selected angle to achieve the desired amount of bend. Typically, the deflector will include at least three channels 51 with additional numbers are also contemplated. Desirably, channels 51 are radially equally distributed about the longitudinal axis 201 of the introducer (e.g., for three members they may be approximately 120° apart). Also, they may be formed in the body 52 of the deflector 50 and run along the length of the deflector from the proximal 53 to distal portions 54 of the deflector. The proximal end 55 of the deflector is desirably shaped to deflect electrode members 30 into the channels 51 as they are advanced through lumen 25. Also channels 51 are desirably sized so that only one electrode member 30 will fit into a channel. In use, these two features confer a self guiding capability to the deflector 50 so that the user can separately or collectively advance the desired number of electrode members 30 into the introducer and have them be guided into separate channels 51. In other embodiments, channels 51 can themselves be deflectable (e.g., through the use of piezo electric or other like materials which can be deflected by electric current) so that user can select and even modify the amount of bend in the deployed members 30. In use, such a feature would allow the user to change the amount of bend in members 30 while observing their position under fluoroscopic or other imaging modality so as to achieve and confirm a desired orientation of the electrode members. Such a feature would also allow the medical care giver to change the direction and orientation of members 30 so as to optimize or tune their detection capabilities to detect a foci F of ANEA in a particular area of the brain.

Figure 7A:
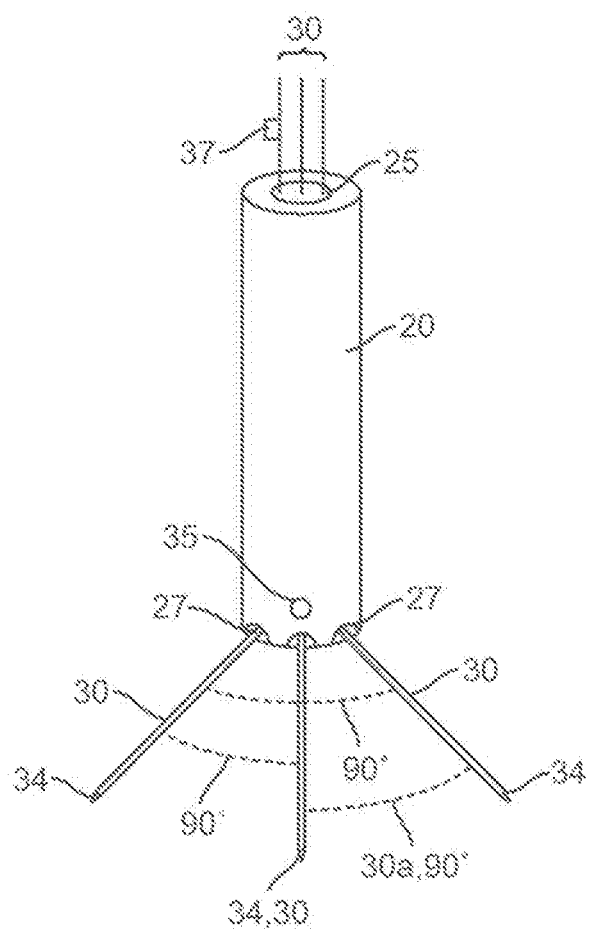
FIG. 7a is a perspective view showing an orthogonal orientation of the electrode members in the deployed state.
Figure 7B:
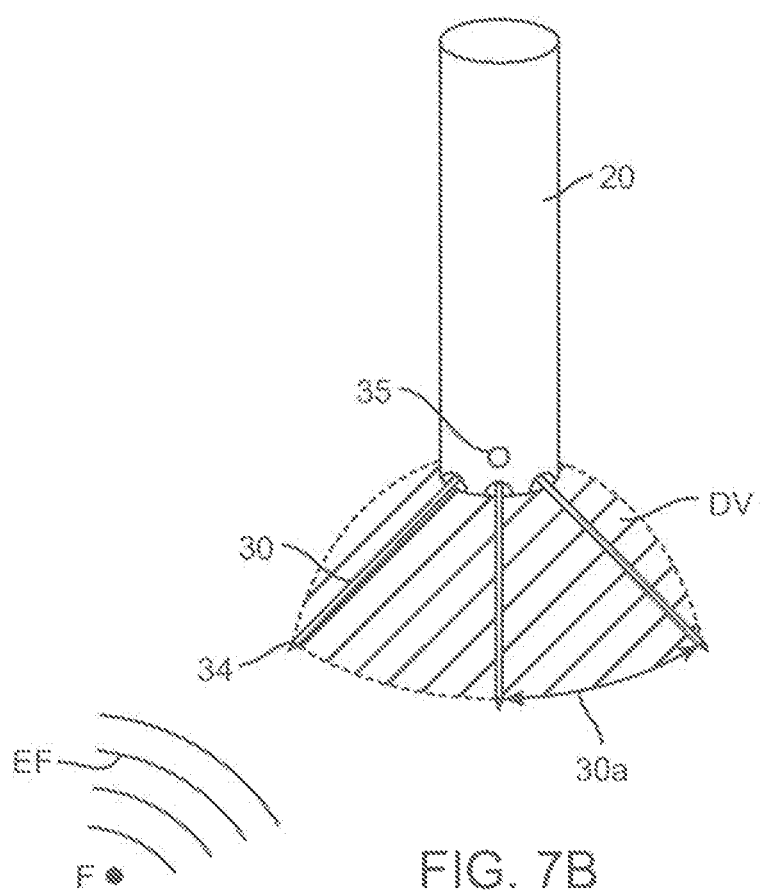
FIG. 7b is a perspective view showing the orientation of the electrode members and the detection volume defined by them in the deployed state.

Referring now to FIGS. 6a, 6b, 7a, 7b, 8a, and 8b, one or more embodiments provide that electrode members 30 have a non-deployed state when positioned in the introducer (as is shown in FIG. 6a) and a deployed state when advanced out of the introducer as shown in FIG. 6b. In the deployed state, the electrode members have an orientation which can detect a foci F of aberrant neural-electric activity. In one embodiment, this is achieved by configuring the electrode members to have a substantially orthogonal orientation with respect to each other. More specifically, with respect to the longitudinal axis 30l of each electrode member, so that the angle 30a between electrode members is approximately 90° so as to define a three dimensional Cartesian coordinate axis system which corresponds to a detection volume DV as shown in the embodiments of FIGS. 7a and 7b. As will be discussed herein, this configuration allows the electrode members to measure voltages produced by an electric field EF generated by Foci F so as derive the electric field vector $\overline{E}$ including the direction and magnitude of the vector. For orthogonal orientations, the defined detection volume DV is substantially tetrahedral is shown in the embodiment of FIG. 7b. Other orientations defining other detection volumes DV are also contemplated such as various polyhedral shapes. For example, four electrode members can be configured to define a substantially pyramidal detection volume. Still additional numbers of electrode members such as six or more can be configured to define a detection volume which approaches a substantially conical shape.

Figure 8A:
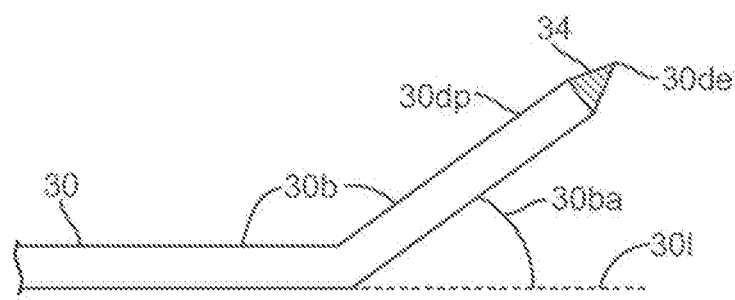
FIGS. 8a and 8b are side views illustrating embodiments of a bent electrode.
Figure 8B:
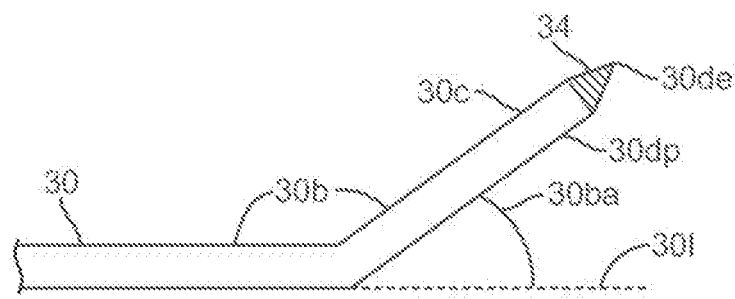

In the non-deployed state within the introducer, electrode members 30 are in a compacted state and substantially straight. As electrode members 30 are advanced out of distal end 22 they become distended so as to define a volume DV for detection of Foci F. The electrode members may include a bent shape 30b when advanced out of introducer 20. This can be accomplished by fabricating the electrode members to have spring memory to assume the bent shape 30b when advanced out of introducer 20. The bent shape 30b can also be accomplished by advancing the electrode members through bent lumens 25 or a deflector 50 as is described herein. The angle 30ba of the bend 30b can be in the range from 20 to 90°, with specific embodiments of 30, 40, 45, 50, 60, 70 and 80°. Bend 30b can be substantially abrupt as is shown in the embodiment of FIG. 8a or can have a selected amount of curvature to confer a curved shape 30c to the deployed portion 30 dp of the electrode member as is shown in the embodiment of FIG. 8b.

Figure 9:
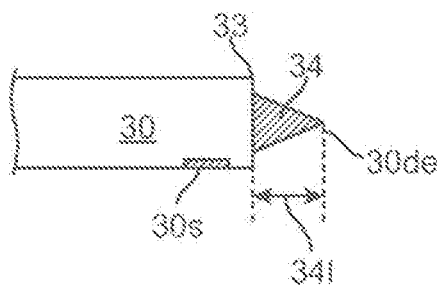
FIG. 9 is a side view illustrating an embodiment of the electrode member including an insulating sleeve and a conductive core.
Figures 10A, 10B:
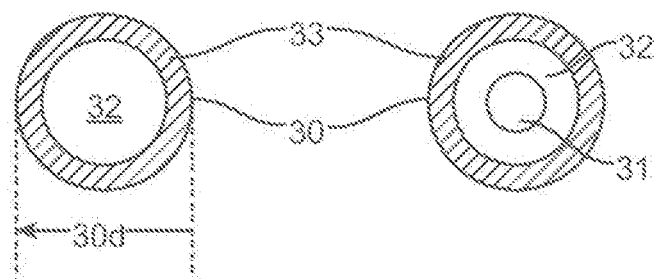
FIGS. 10a-10b are cross sectional views of embodiments of the electrode member.

Referring now to FIGS. 9, 10a, and 10b, typically, the electrode members 30 will comprise a conductive core 32 and an outer insulating sleeve or jacket 33 extending along most of the length of the electrode member so that the only tissue contacting conductive portion 34 of the electrode member is the distal end 30de. The length 34l of the conductive portion 34 will be 1 mm or less, though longer portions are also contemplated. In one or more embodiments, the length is in the range from about 0.75 to about 0.25 mm. The insulating sleeve 34 can comprise various insulating biocompatible polymers known in the art such as silicone and polyurethane. Sleeve 34 can also have lubricous properties to facilitate advancement of the electrode members into tissue. Also, sleeve 34 can contain various drug eluting compounds known in the art to reduce bio-adhesion to the sleeve (both cells and molecules). The conductive core 32 of the members 30 can be fabricated from various biocompatible conductive materials known in the art including metals and conductive polymers and like materials. An example of a suitable metal includes 304V steel. In preferred embodiments, members 30 comprise a shape memory material such as NITINOL. For particular shape memory embodiments, the advanced electrode members 30 can assume their deployed state as they are warmed by the brain tissue above the transition temperature of the selected shape memory material.

In many embodiments, the distal ends 30de of the electrode members have a pointed or other tissue penetrating shape to facilitate advancement into tissue. Also, desirably, electrode members 30 have sufficient stiffness to be advanced into tissue, but are sufficiently flexible to assume a curved shape when advanced out of the introducer. The stiffness and flexibility can be achieved by selection of the member diameter, material and material treatment (e.g., annealing) as is known in the medical guide-wire arts. In various embodiments, the diameter 30d of the electrode members can be in the range of 0.0005 to 0.018" with specific embodiments of 0.001, 0.005, 0.010 and 0.015". Typically, the electrode member 30 will be solid as is shown in the embodiment of FIG. 10a; however, in various embodiments, members 30 may have a lumen 31 as is shown in the embodiment of FIG. 10b. Lumen 31 can be used for intracranial delivery of one or more medications. In such embodiments, members 30 can be fabricated from various hypotubes known in the art. Also in various embodiments members 30 may also include one or more sensors 30s for measuring various tissue properties which may be predictive of seizure or pre-seizure events. Accordingly, such sensors can include without limitation, pH, temperature, $pO_2$, $pCO_2$, glucose, and other biochemical related sensors. Measurements from such sensors can be combined with voltage/electric field vector measurements as means for determining pre-seizure and seizure events.

Figure 11:
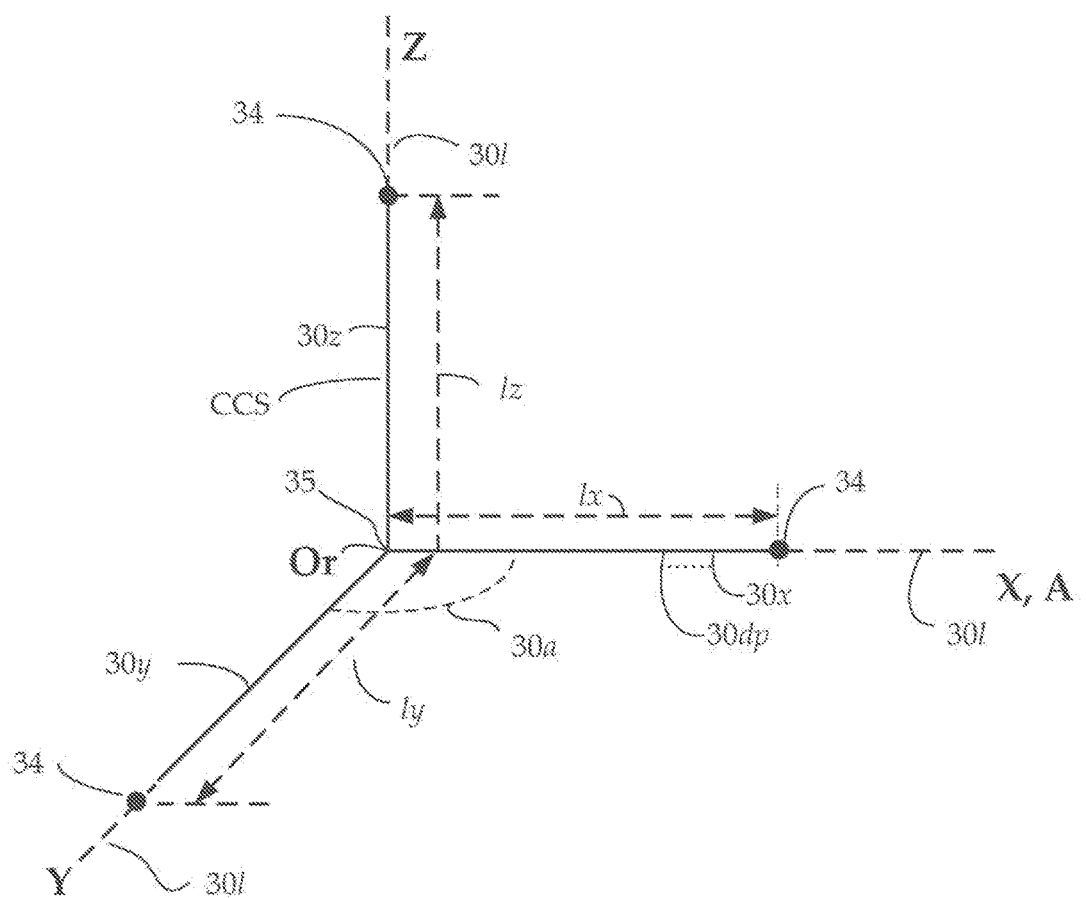
FIG. 11 is a graphical view illustrating alignment of the electrode members with a Cartesian coordinate system.
Figure 12:
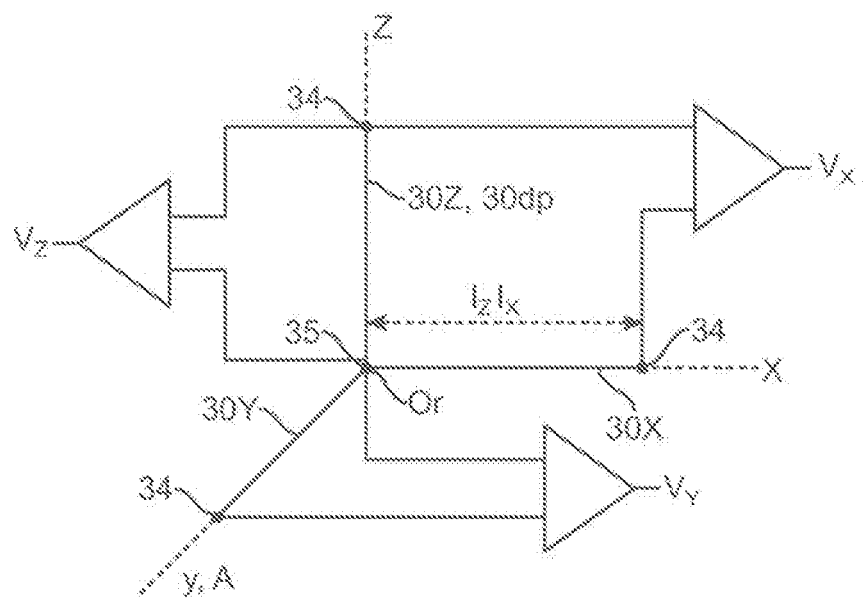
FIG. 12 is a combination graphical and schematic view illustrating alignment of the electrode members with a Cartesian coordinate system and generation of voltages the electrode members as a result of abnormal neural-electric activity.

Referring now to FIGS. 11-12, in many embodiments, the deployed portions 30dp of the electrode members 30 (i.e., that projecting out of the introducer 20) can have a substantially orthogonal orientation such that each electrode member 30 is oriented with an axis A of a Cartesian coordinate system CCS. The origin or of the axes corresponds to the position of reference electrode 35 which typically will be at the distal end 22 (FIG. 6a) of introducer 20. This results in an x, y and z electrode member 30x, 30y and 30z. Each of these oriented electrode members project a selected distance l past reference electrode 35 resulting in distances $I_x$, $I_z$ and $I_z$ which in preferred embodiments are substantially the same. The electric field EF (FIG. 7b) generated by Foci F results in voltages $V_x$, $V_y$ and $V_z$ at respective electrode members 30x, 30y and 30z. The actual voltage being due to the potential difference between tissue contacting conductive portion 34 and reference electrode 35 which is typically positioned near introducer distal end 22). In many embodiments, electrode members 30x, 30y and 30z can share a common reference electrode 35 or each may have its own.

Figure 13:
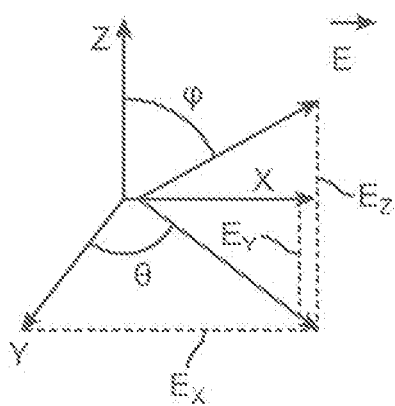
FIG. 13 is graphical view illustrating an electric field vector produced by aberrant neural-electric activity and its polar components.

A discussion will now be presented of the mathematical methods used to calculate the components of the electric field vector $\overline{E}$ generated by a foci F of abnormal neural-electric activity and the subsequent direction D of foci F relative to the distal end the introducer. These and other related methods along with equations 1-6 can be incorporated into algorithms 83 described herein. Referring now to FIGS. 11-13 and equations 1-6 below, electric field vector $\overline{E}$ has a magnitude E having scalar components $E_x$, $E_y$ and $E_z$ and angular directions θ and φ. Measurement of voltages $V_x$, $V_y$ and $V_z$ by electrode members 30x, 30y and 30z allows calculation of $E_x$, $E_y$ and $E_z$ using equation (1), the magnitude of the vector $\overline{E}$ can be calculated by equation (2). Equations 4-6 allow determination of the direction of vector $\overline{E}$ relative to origin Or (and hence the direction relative to introducer distal end 22) by virtue of determination of angles φ, and θ. Determination of this direction, then allows determination of the direction D of Foci F (relative to introducer distal end 22) from which vector $\bar{E}$ emanates.

$$E_x = V_x/I_x, I_y = V_y/I_y, \text{ and } E_z = V_z/I_z \qquad (1)$$

$$|\bar{E}| = (E_x^2 + E_y^2 + E_z^2)^{1/2} \qquad (2)$$

$$\cos \varphi = (E_z/|\bar{E}|) \qquad (3)$$

$$\varphi = \cos^{-1}(E_z/|\bar{E}|) \qquad (4)$$

$$|\bar{E}|*\sin \varphi * \cos \theta \qquad (5)$$

$$\theta = \cos^{-1}(|\bar{E}|*\sin \varphi)/E_y \qquad (6)$$

Figure 14:
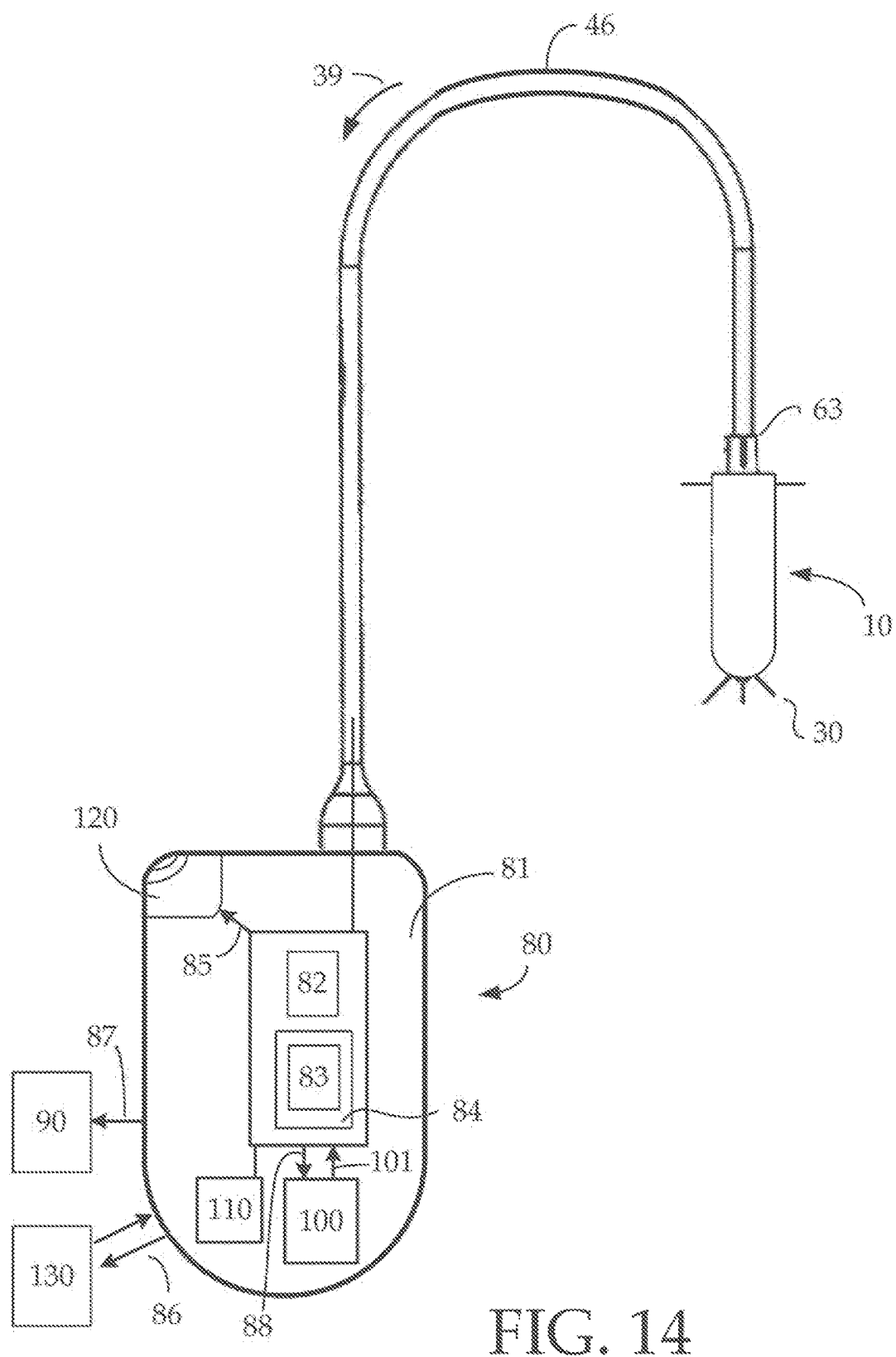
FIG. 14 is a block diagram showing an embodiment of a control module for use with various embodiments of the ANEA detection apparatus.
Figure 15:
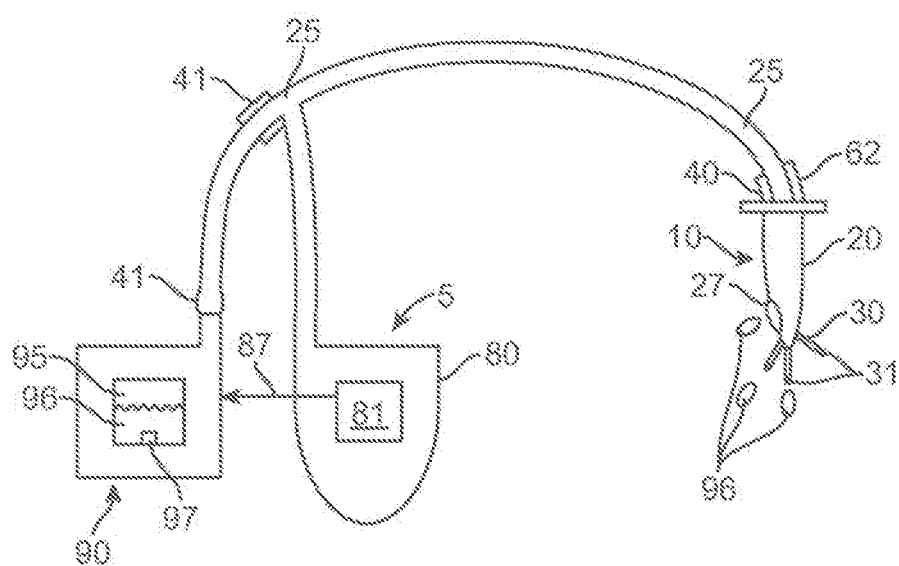
FIG. 15 is a block diagram/side view of an embodiment of the drug delivery device.
Figure 16A:
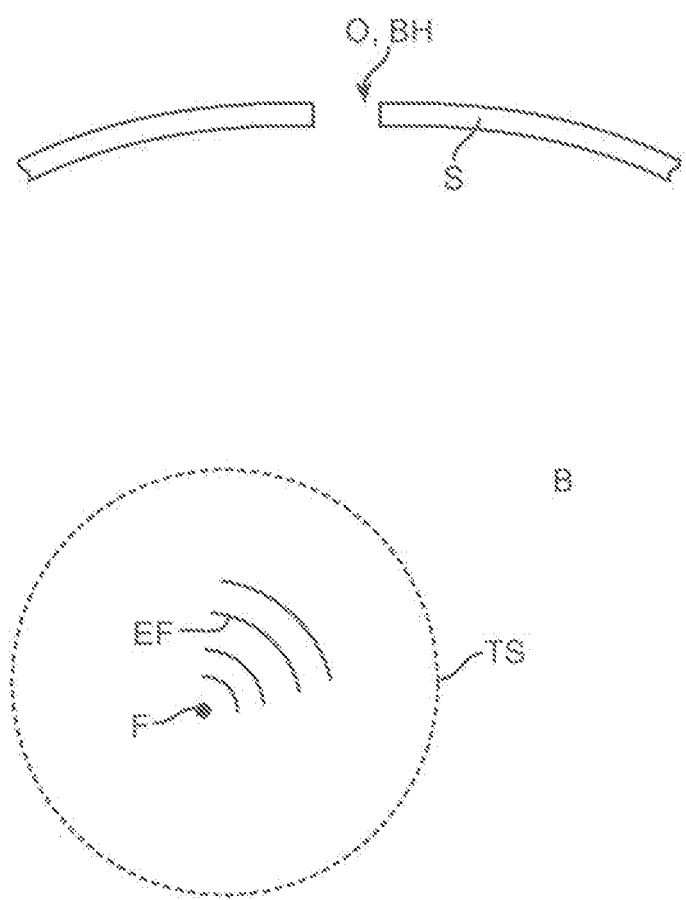
FIGS. 16a-16e are side views illustrating a method for introduction of the introducer and deployment of the electrode members to detect a Foci of aberrant neural electric activity in a target tissue site in the brain.
Figure 16B:
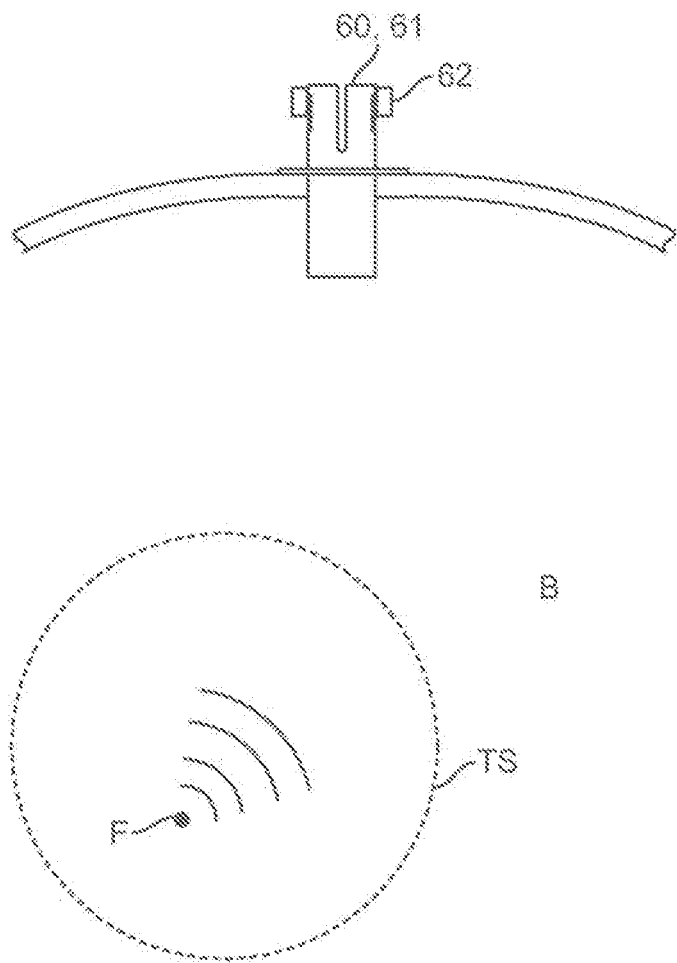
Figure 16C:
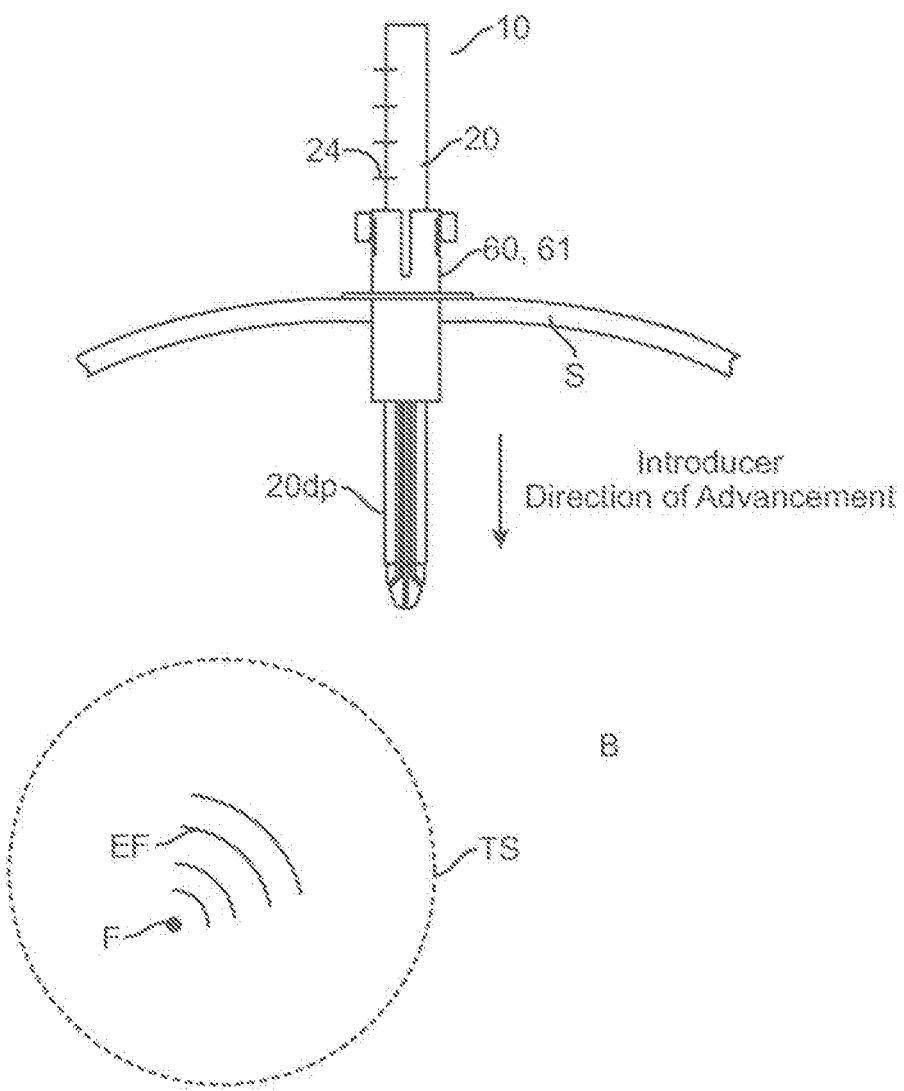
Figure 16D:
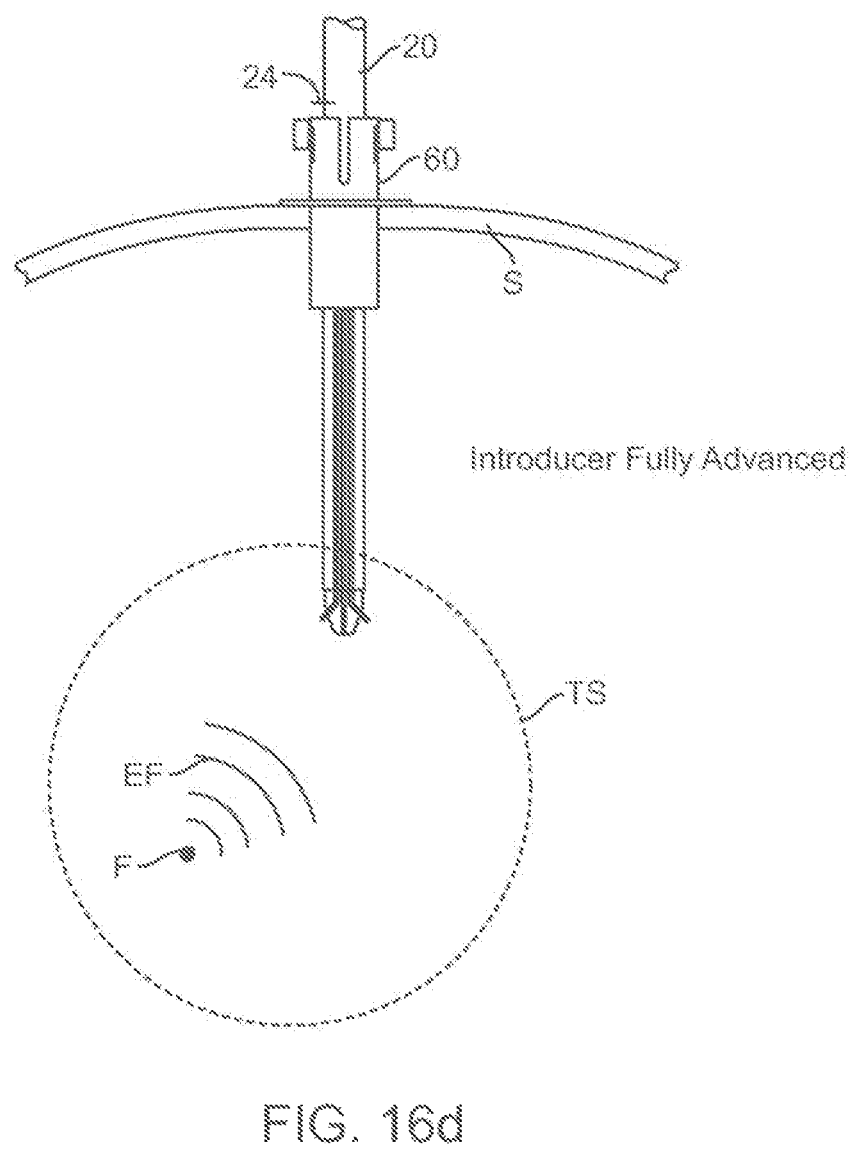
Figure 16E:
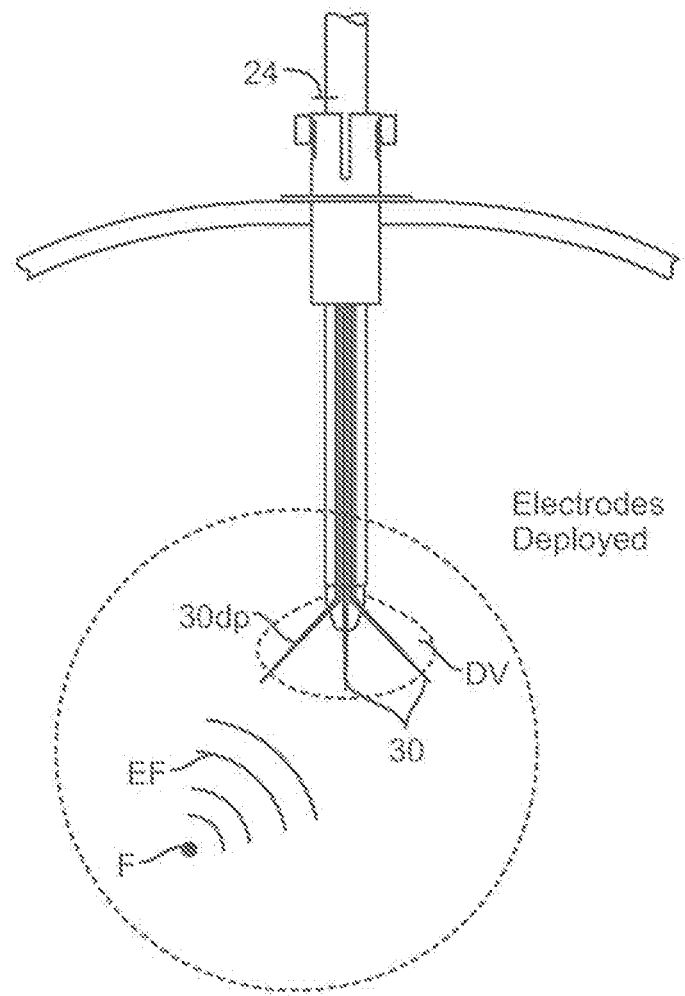

Referring now to FIG. 14-15, in many embodiments, apparatus 10 can be coupled to a control module 80 (see FIG. 1) (hereinafter module 80) that is configured to perform one or more functions. These can include storage and analysis of signals received from electrode members 30, sensors 63, detection of a pre-seizure or seizure event, alerting the patient and medical care provider of an impending seizure and control of various interventional actions to prevent a seizure including drug delivery and electrical stimulation of brain tissue. Module 80 can include one or more processors, state devices, circuits (e.g., power control, filters, etc.) alarms, batteries and other power storage devices. It can also include one or more communication resources 110 such as an RF communication chip for wirelessly communicating with external medical monitoring instrumentation using MICS or other medical wireless communication protocol. Module 80 may also include an integral drug delivery device 90 as well as brain stimulator 100 described herein. Control module 80 can be worn by the patient or may be configured to be implanted subcutaneously in the head and neck area (as shown in FIG. 2a) or other area in the body.

Module 80 will typically include at least one controller 81 which can comprise various logic resources 82 such as a processor, state device or a combination of both. Processor 82 can be off-the-shelf (e.g., such as those manufactured by Intel® or Texas Instruments®) or can comprise a custom chip such as an ASIC. Controller 81 may include one or more algorithms 83 which can be implemented through software, hardware or a combination of both. For software implementation, algorithms 83 can be stored in memory resources 84 (e.g., ROM, RAM, DRAM, etc) integral or coupled to logic resources 82. Algorithms 83 can be configured to perform a number of functions including without limitation: processing and storage of signals 39 received from electrode members 30; sensors 30s or 63, calculation of the components of an Electric Field vector $\bar{E}$ including the magnitude and direction D of the vector, detection of one or more of ANEA, a pre-seizure or seizure event; alerting the patient and medical care provider of an impending seizure and communicating with external medical monitoring instrumentation; and control of various interventional devices and actions to prevent a seizure such as drug delivery and electrical stimulation of brain tissue. As is described herein, various detection algorithms 83 can be configured to generate a detection score indicative of whether a pre-seizure or seizure event is occurring. Algorithms 83 can be configured to include one or more signal processing algorithms known in the art such as Fast Fourier Transforms, wavelet, fuzzy logic and like algorithms.

In many embodiments, module 80 includes a stimulator device or stimulator 100 configured to send an inhibitor signal 101 via electrode members 30 (or other implanted electrode) to prevent the onset of a seizure or stop an occurring seizure or otherwise reduce its duration. Stimulator 100 will typically comprise power control and charging circuitry and a discharging capacitor or other dischargeable power voltage source. It can also include various pacing and/or signal processing circuits to as to provide a duty cycle of inhibitory signals over an extended period of time.

Drug delivery device 90 can comprise one or more drug pumps known in the art including, displacement pumps (e.g., a piston pump), peristaltic pumps, screw pumps and like devices. It can be miniaturized for implantation in the head or neck area or other portion of the body. Miniaturized pumps can comprise MEMS and/or bubble jet based miniature pumps. Also it can be configured for one or both of intracranial or IV delivery. For intracranial delivery device 90, can be fluidically coupled to one or more lumens 25 of introducer 20 via fluidic connectors 40, 41 so as to deliver the drug through lumen 25 and/or through lumens 31 of hollow embodiments of electrode members 30. Connectors 41 can include, luer-lock, connectors, Touhy Borst adapters and other like devices. Delivery device 90 can also be configured for the delivery of liquids, solids or both. For liquid delivery, the device can use one or more of displacement, rotary or peristaltic pumping devices. For solid delivery, a miniature screw pump can be used. Typically, the device 90 will also include a reservoir 95 containing one or more medicaments 96. However, reservoir 95 can also be separate from delivery 90 though still coupled to it fluidically via a catheter or like connecting member. In the later case, the reservoir can be implanted subcutaneously or can even be positioned external to the body to allow for replenishment of drug (e.g., via injection through the skin). Delivery device 90 is also desirably configured to be controlled by signals 87 from module 80 and controller 81. Reservoir 95 can also include one more sensors 97 configured to sense the amount of drug (liquid or solid) remaining in the reservoir as to alert the patient or doctor when the reservoir needs to be replenished.

Referring now to FIGS. 2b and 16a-e, a method of introducing introducer 20 and deploying electrode members 30 will now be discussed. Prior to introduction of apparatus 10, a patient having epilepsy or other condition characterized by ANEA can undergo a series of EEGs or other related brain scans to determine the location and other characteristics of a foci of ANBNEA likely causing the condition to be treated. This information can then be used to determine the target tissue site TS for deployment of the electrode members and thus the corresponding site in the skull for the introduction of the introducer. In many cases, the introducer can be introduced through a burr hole plug; however, it will be appreciated this is exemplary and that other approaches are equally applicable. After the burr hole BH has been drilled and burr hole plug 61 is positioned, the introducer is advanced into brain tissue to the desired target tissue site TS. The advancement can be done under flouroscopic or other form of medical imaging observation. Positioning of the distal tip 22 of the introducer at the desired target site TS can be facilitated by the use of a distal tip marker on the introducer. Additionally, the introducer can include graduation markings 24 along its length indicating the depth of insertion. Once inserted the desired depth, the surgeon can then lock the introducer in place using locking device 62. Determination that the introducer has been locked in place can be achieved through a signal sent by, for example, contact sensor 63.

Electrode members 30 can then be deployed to achieve a detection volume DV having a selectable size and shape. The electrode members 30 can be deployed individually, or collectively. They can also be advanced by hand or using an advancement member 28 (coupled to the proximal portions of the members 30) or by other advancement means known in the art. Depth of insertion of the electrode members can be controlled by, for example, using a stop placed on advancement member 30 (not shown) and/or by means of a stop 37 (FIG. 3) placed on each electrode member 30. Deployment of members 30 can also be guided by flouroscopic observation or other imaging modality. In some embodiments, this process can be facilitated by superimposing onto the flouroscopic image (or other image) a marker or other indicia denoting the likely location of the foci F of ANEA. This physician can use this marker to locate and orient the position of the deployed electrode members so as to optimize the detection of ANEA signals from Foci F. For example, the physician can use the marker to deploy the electrode members such that their distal ends are placed within a selectable distance of Foci F. Also, it can be used to achieve a selectable angular orientation, e.g., 90°, with the longitudinal axis of one or more of the electrode members so as to maximize the voltage produced at those electrode members from an electric field vector generated by ANEA signals from foci F.

After deployment of the electrode members, the physician can perform one or more tests to ascertain that the electrode members are functioning and capable of detecting ANEA signals from one or more foci F. This can include sending a test signal from a separate electrode (not shown) positioned in the brain so as to have the same directional orientation with respect to the electrode members as Foci F does. The test signal can be configured to simulate the amplitude and frequency of an actual ANEA signal. If the electrode members are not able to detect the test signal, the physician can redeploy all or a portion of the electrode members until he or she gets the desired response. In particular embodiments, the test signal can not only be used to test the functionality of the deployed electrode members, but also as a beacon to assist in their deployment. In such embodiments, the physician can deploy and position the electrode members while the test/beacon signal is being sent so as to maximize the resulting voltages measured by the electrode members. After the electrode members 30 are correctly deployed, the electrode members can be locked in place using locking device 63 or another locking mechanism. The burr plug will then be sealed/closed using standard methods known in the art and connectors 40 (FIG. 6a) can be connected to control module 80 (or other like device) via one more wires or the connection can be wirelessly. The control module 80 can be implanted subcutaneously in the head and neck area or can be worn by the patient. In embodiments where module 80 contains a drug delivery device 90 for treating the foci F of ANEA, the module will typically be implanted subcutaneously in the head and neck area. In embodiments where it does not, it can positioned in any number of location or can be worn by the patients. In such embodiments, a separate drug reservoir and drug delivery device can be implanted in the head and neck so as to provide for intracranial delivery of the drug. Alternatively, the drug can be delivered intravenously (IV) in which case the reservoir and drug delivery device can be positioned at any number of locations and/or externally worn by the patient. In embodiments where a combination of intracranial and IV delivery are used, a drug reservoir/delivery device can be implanted in the head and neck areas and another delivery device/reservoir can be worn by the patient for IV delivery.

Figure 17A:
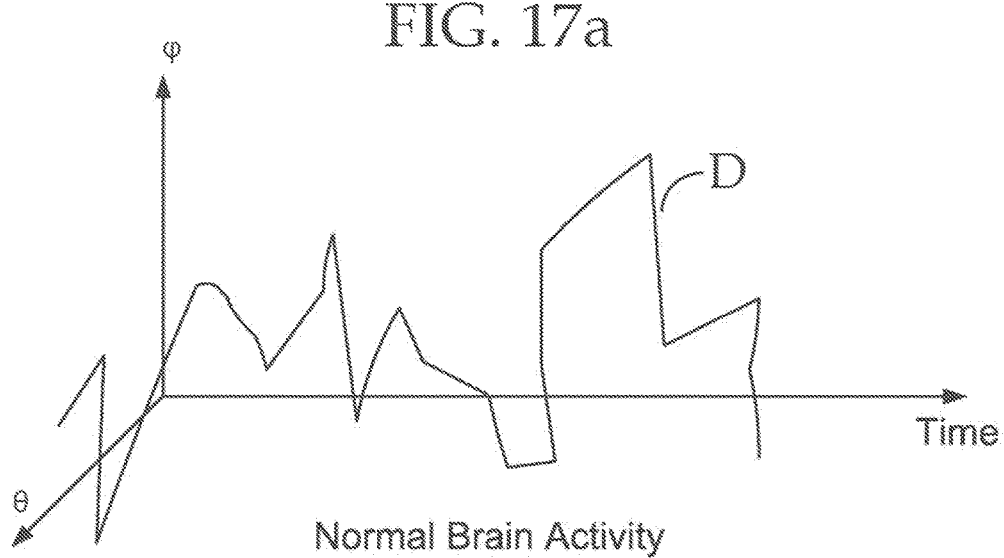
FIGS. 17a and 17b are 3d plots of the direction of an electric field vector over time in the brain.
Figure 17B:
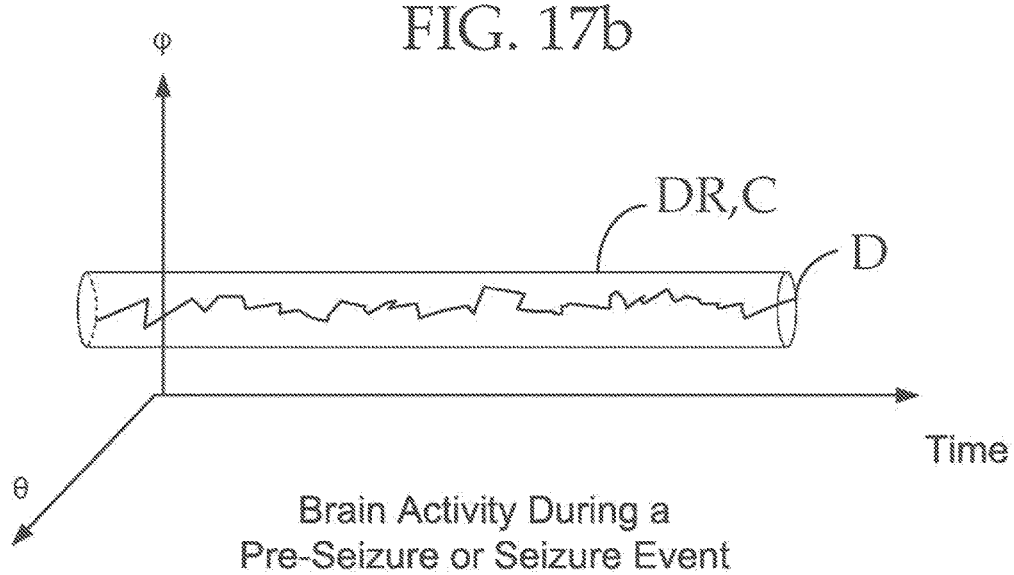
Figure 18:
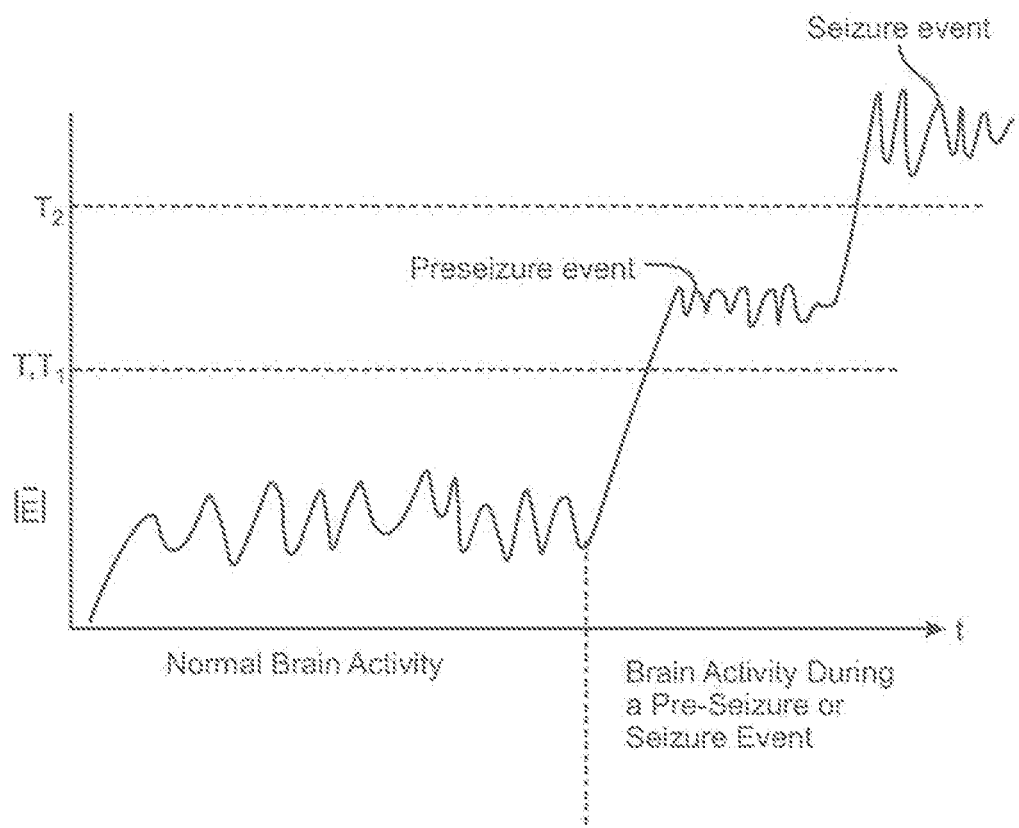
FIG. 18 is plot of the amplitude of an electric field vector over time during periods of normal and aberrant neural-electric activity in the brain.

A discussion will be presented of methods of detecting ANEA using apparatus 10 and utilizing this information to detecting a neurological event or condition such as a seizure. In these and related embodiments, methods will be presented for detecting both a pre-seizure event and a seizure event (such events can correspond to pre-seizure and seizure states). For ease of discussion, the pre-seizure and seizure events will refer to an epileptic pre-seizure event (also as a pre-ictal state or event) and epileptic seizure event (hereinafter seizure); however, it will be appreciated that these methods are applicable to detecting pre-seizures events/states and seizures associated with other neurological events or conditions and syndromes such as migraines headaches and other related conditions. As discussed above, apparatus 10 measures electric field vectors in the brain generated by neural activity by measuring the voltage differential between each electrode member 30 and the reference electrode 35 and using these values to calculate electric field vector $\bar{E}$. Various characteristics of field vector $\bar{E}$ can then be used as an indicator of a seizure or pre-seizure event. Referring now to FIGS. 17-18, during normal brain activity, the electric field vector $\bar{E}$ will typically have a random direction D (as defined by angles $\varphi$ and $\theta$ described above) as is shown in FIG. 17a. Also during normal activity, the magnitude/amplitude $|\bar{E}|$ of the electric field vector will be random but will have a time average value which stays below a particular threshold T as is shown in FIG. 18. In contrast, during a period of aberrant neural-electric activity such as that occurring during a pre-ictal event or a seizure event, electric field vector $|\bar{E}|$ will dwell in a particular direction D or directional region DR for an extended period of time compared to normal brain activity as is shown in FIG. 17b. The dwell time can be tenths of a second to several seconds or longer (e.g., 0.10 to 10 seconds with specific embodiments of 0.2, 0.5, 1, 2, and 5 seconds) shorter dwell times are also contemplated (e.g., 0.01 to 0.1 seconds). During a pre-seizure or seizure event, the directional region DR will be bounded by a cylinder C or related geometric shape. Also, the electric field amplitude will exceed a threshold T above normal activity for a sustained period of time as is shown in FIG. 18. This can include exceeding a first threshold $T_1$, for a pre-seizure or other like event and a second threshold $T_2$, for a seizure or other like event.

In particular embodiments, algorithms 83 resident within module 80 can use one or more of the above changes in electric field vector characteristics (e.g., in amplitude and direction of the field vector) to detect a period of ANEA indicative of a pre-ictal event, epileptic seizure or other seizure event (such periods of ANEA can thus be used as a marker of a pre-ictal event, epileptic seizure or other seizure event). For example, a pre-ictal event or seizure may be detected based on the electric field vector staying in a particular direction or directional cone for longer than a selected period of time. For applications where the location of a known foci of ANEA has previously been determined prior to placement of apparatus 10, additional algorithmic weightings can be employed if the direction of the detected electric field vector is within a selected directional cone that includes the direction of the previously detected Foci F (this direction being the direction of the foci relative to distal end of the introducer).

In another example of a predictive electric field vector characteristic, a pre-ictal event or seizure may also be detected based on whether the electric field amplitude exceeds a particular threshold and more preferably, whether the time average of the electric field amplitude exceeds the threshold. A combination of these two approaches can also be used so that the direction and amplitude of the electric field vector both need to exceed threshold values. Additionally, pattern recognition algorithms can be employed to detect particular signal patterns in the electric field which are indicative of a pre-ictal event or seizure (also known as a seizure event). A data base of such patterns can be generated from EEG measurements taken from the patient themselves, an epileptic patient population or a combination of both. Again, the detection algorithm can employ both pattern detection with one or both of electric field amplitude and direction so to make a determination of pre-ictal event or seizure. A detection score exceeding a certain threshold can be used to predict a pre-ictal event or seizure, with a score over a first value indicative of a pre-ictal event and a score over a second value indicative of a seizure. Also, weightings can be assigned to these or other detection parameters so that algorithm generates a detection score value as a function of these parameters. Weightings can be chosen from a weighting database taken from a patient population or they can be established for each individual patient by monitoring the patient over a period of time using external EEG electrodes or with apparatus 10 in place and then inducing a pre-seizure or mild epileptic seizure and recording the data for the these detection parameters. The weightings can also be updated after subsequent pre-ictal events or seizure either manually by a health care provider or by algorithm itself using self learning methodology.

When the detection score exceeds a threshold value indicative of a pre-ictal event or seizure event, module 80 can perform one or more functions. First, now referring to FIG. 14, the module can send a signal 85 to an alarm 120 to alert the patient so that they can take precautionary measures such as taking medication as well as sitting or lying down or discontinuing any hazardous activities. It can also send a wireless signal 86 (via a RF or IR port to a monitoring device 130 in a hospital or doctor's office (this can be achieved using a cellular phone or various medical telemetry devices known in the art). It can also send a signal 87 to a drug delivery device 90 to deliver a dose of an anti-seizure medication and/or a signal 88 to a stimulating device 100 to send an inhibitor signal 101 via electrode members 30 (or other implanted electrode) to prevent the onset of a seizure or stop an occurring seizure. In various embodiments, a combination of both interventions can be used. Inhibitory signal 101 can have various forms. In one embodiment, it can be configured to depolarize the regions of the around the Foci F causing the pre-ictal event or seizure. In other embodiments, it can be matched to the particular pattern of aberrant neural-electric activity causing the pre-ictal event or seizure so as to be out of phase with the aberrant neural-electric activity or otherwise dampen its effect on surrounding tissue. In preferred embodiments, the inhibitory signal is delivered using electrode members 30 as stimulating electrodes 36; however, the use of separate electrodes as stimulating electrodes is also contemplated.

For embodiments employing drug intervention, the delivered dose of drug can be titrated based upon the value of the detection score and/or whether the detected event is a pre-ictal event or a seizure. A baseline dosage can be determined based upon various patient parameters, such as weight, age, type of epilepsy (e.g., partial-onset seizure). Suitable anti-seizure medications include phenytoin sodium (Dilantin), furosemide or other loop diuretic, with other anti-seizure medications known in the art also contemplated. During and after drug delivery, system 10 can be configured to continue to monitor brain activity to determine if the pre-ictal event or a seizure has subsided and to what degree. Repeat dosages of drug can be administered as needed depending upon the detection score or other factor. Increased dosages can be given if the detection score remains above a selected level. Also, selectable dosing regimens can be used depending upon one or more of the detection score, type of epilepsy, pattern of seizures, age, weight, etc. For example, for a pre-ictal event, a bolus dose could be given intracranially, whereas for full seizure, treatment could include intracranial bolus dose followed by a longer term maintenance dose (either IV or intracranial) of the same or even a second drug for a selectable period of time post-seizure. Also in various embodiments, a selectable dosing regimen can be delivered based not only on a individual detection score but also based on a time pattern of detection scores, even if the scores are below a pre-ictal event or seizure event threshold. For example, a dose of drug could be delivered based upon a certain number of spikes in the detection score over a selected period of time. Various dosing regimens can also be configured to use a combination of intracranial and IV administration using an intracranial delivery device and an IV pump.

In various embodiments, the dosing regimen can be tailored to the particular drug or combination of drugs delivered. For use of furosemide or other like drug, the dosing regimen could be in the form of a bolus dose configured to achieve a selected peak intracranial concentration with a subsequent maintenance dose of the same or different drug. In particular embodiments including use of multiple seizure drugs, the detection score can also be used to determine what drugs are actually given. For example, a detection score above a first threshold can be used for a first drug and another detection score above a second threshold can be used to select a second drug.

In various other embodiments of methods for detecting aberrant neural-electric activity causing a seizure or pre-seizure event, changes in tissue impedance can also be used with such changes being measured by electrode members 30. Such approaches operate on the principle that the impedance of brain tissue changes during a pre-seizure or seizure state. Tissue impedance can be measured by applying a slight voltage or current between conductive portion 34 (FIG. 6b) and reference electrode 35. Both real and the imaginary component of impedances can be used. Similar to methods employing voltage/electric field vector measurements, measured impedances can be used to generate detection score as mean do predict both pre-seizure and seizures events. In particular embodiments, impedance measurements can be combined with voltage/electric field vector measurements to further improve the sensitivity for predicting both pre-seizure and seizures events FIGS. 19A and 19B illustrate side views of an ANEA detection apparatus utilizing individually advanceable electrode members to obtain a selectable detection volume, under an embodiment. FIG. 19A illustrates an embodiment in which three electrode members are individually advanced out of an introducer, while three electrode members are contained within an introducer. FIG. 19B illustrates an embodiment in which six electrode members are advanced out of the introducer in a deployed state. In the embodiment of FIG. 19A the non-deployed electrode members may be stored in various states (e.g., a compacted state). A detection apparatus as illustrated in FIGS. 19A and 19B includes elements (e.g., introducer 20; electrode members 30) as discussed with respect to drawings FIG. 1 through FIG. 18. In the illustration of FIG. 19A, three of the six electrode members 30 are individually extended to form a substantially orthogonal orientation with respect to each other, while the remaining three electrode members are not extended. For example, the non-extended electrode members are contained in the introducer 20. More specifically, with respect to the longitudinal axis 30*l* of each extended electrode member, the angle 30*a* between the electrode members is approximately 90° so as to define a three dimensional Cartesian coordinate axis system which corresponds to a detection volume DV. In the illustration of FIG. 19B, all six electrode members 30 are extended from introducer 20, so that their deployed states define a detection volume which approaches a substantially conical shape. While the ANEA detection apparatus of FIG. 19A and FIG. 19B utilizes six electrode members, additional electrode members can be utilized and selectively extended to form a substantially conical detection volume. Furthermore, in implementations specific mechanisms may be utilized with the ANEA detection apparatus of FIGS. 19A and 19B to individually or collectively advance the electrode members and obtain a selectable detection volume. For example, a deflector may be utilized (e.g., as discussed with respect to FIGS. 4A, 4B, 4C and 5) so that a user can separately or collectively advance the desired number of electrode members 30. Additionally or alternatively separate lumens may be provided for each electrode member 30 to provide for the independent advancement of the electrode members 30.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments can be sized or otherwise adapted for various pediatric applications or the treatment of any number of neurological event or conditions involving aberrant neural-electric activity.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An apparatus for detection of aberrant neural-electric activity in a brain, the apparatus comprising:
an introducer configured to be introduced into brain tissue, having a proximal end configured to be coupled to an electrical connector, and a distal end including a plurality of lumens with a port coupled to each lumen; and
three electrode members individually extendable from the plurality of lumens, wherein the three electrode members form a group of electrode members, wherein each of the electrode members is extendable to define a different axis of a Cartesian coordinate system with a respective origin at the distal end of the introducer;
wherein each of the electrode members has an insulated proximal portion and an exposed distal portion, each electrode member having a non-deployed state and at least one deployed state in which the electrode member is extended, the exposed distal portion of the electrode member having a bend when the electrode member is in the at least one deployed state;
wherein the three electrode members are extendable into corresponding deployed states in which the bends of the three electrode members are such that the exposed distal portions define a substantially orthogonal shaped detection volume for determining a location of a foci of aberrant neural-electric activity within the brain relative to the deployed electrode members; and
a control module, wherein the control module includes a stimulator device, the stimulator device configured to send an inhibitor signal via the three electrode members to prevent an onset of an epileptic seizure.

2. The apparatus of claim 1, further comprising a plug configured to be inserted into a burr hole in a skull, the plug having a lumen for insertion of the introducer.

3. The apparatus of claim 2, further comprising a locking device engageable with the plug, the locking device configured to lock the introducer to the plug.

4. The apparatus of claim 1, wherein the aberrant neural-electric activity is a preceding event to the epileptic seizure.

5. The apparatus of claim 1, wherein the electrode members are configured to determine an electric field vector generated by the aberrant neural-electric activity.

6. The apparatus of claim 1, wherein the electrode members comprise a shape memory material.

7. The apparatus of claim 1, wherein a stiffness of the electrode members is configured to substantially maintain a size and shape of the detection volume after the electrode members are advanced into the brain tissue.

8. The apparatus of claim 1, wherein a stiffness of each of the electrode members and a shape of each of the electrode members in the at least one deployed state are configured to maintain a position of the electrode members in the brain tissue.

9. The apparatus of claim 1, wherein a stiffness of the electrode members and a shape of the electrode members in the at least one deployed state are configured to substantially anchor and/or stabilize a position of the electrode members in brain tissue.

10. The apparatus of claim 1, wherein a size and shape of the electrode members in the at least one deployed state are configured to have a minimal physiologic effect on the brain tissue in which they are deployed.

11. The apparatus of claim 1, wherein a length of each of the electrode members advanced into the brain tissue is from about 03 cm to about 15 cm.

12. The apparatus of claim 1, wherein a length of each of the electrode members advanced into the brain tissue is from about 01 cm to about 03 cm.

13. The apparatus of claim 1, wherein a length of each of the electrode members advanced into the brain tissue is about 01 cm.

14. The apparatus of claim 1, further comprising a reference electrode positioned at a distal portion of the introducer.

15. The apparatus of claim 1, wherein, for each electrode member, for each at least one deployed state, the bend of that electrode member in that deployed state is different from the bend of the electrode member in other deployed states of the at least one deployed state.

16. The apparatus of claim 1, wherein the inhibitor signal can be configured to depolarize a region around the foci.

17. The apparatus of claim 1, wherein the inhibitor signal can be configured to be matched to a particular pattern of aberrant neural-electric activity causing a pre-ictal event or epileptic seizure so as to be out of phase with the aberrant neural-electric activity.

18. An apparatus for detection of aberrant neural-electric activity in a brain, the apparatus comprising:
  an introducer configured to be introduced into brain tissue, having a proximal end configured to be coupled to an electrical connector, and a distal end including a plurality of lumens with a port coupled to each lumen; and
  three electrode members individually extendable from the plurality of lumens, wherein the three electrode members form a group of electrode members, wherein each of the electrode members is extendable to define a different axis of a Cartesian coordinate system with a respective origin at the distal end of the introducer;
  wherein each of the electrode members has an insulated proximal portion and an exposed distal portion, each electrode member having a non-deployed state and at least one deployed state in which the electrode member is extended; and
  wherein the three electrode members are extendable into corresponding deployed states in which the exposed distal portions define a substantially orthogonal shaped detection volume for determining a direction of a foci of aberrant neural-electric activity within the brain relative to the deployed electrode members; and
  a control module, wherein the control module includes a stimulator device, the stimulator device configured to send an inhibitor signal via the three electrode members to prevent an onset of an epileptic seizure.

19. The apparatus of claim 18, wherein the inhibitor signal can be configured to be matched to a particular pattern of aberrant neural-electric activity causing a pre-ictal event or epileptic seizure so as to be out of phase with the aberrant neural-electric activity.

\* \* \* \* \*